(12) United States Patent
Farrand

(10) Patent No.: US 7,771,800 B2
(45) Date of Patent: Aug. 10, 2010

(54) CHIRAL COMPOUNDS

(75) Inventor: Louise Diane Farrand, Dorset (GB)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 12/088,470

(22) PCT Filed: Sep. 20, 2006

(86) PCT No.: PCT/EP2006/009133

§ 371 (c)(1),
(2), (4) Date: Mar. 28, 2008

(87) PCT Pub. No.: WO2007/039104

PCT Pub. Date: Apr. 12, 2007

(65) Prior Publication Data

US 2008/0272337 A1 Nov. 6, 2008

(30) Foreign Application Priority Data

Sep. 30, 2005 (EP) ................. 05021491

(51) Int. Cl.
*C09K 19/58* (2006.01)
*C09K 19/38* (2006.01)
*C09K 19/34* (2006.01)
*C09K 19/32* (2006.01)
*C07D 321/10* (2006.01)
*C09K 19/20* (2006.01)

(52) U.S. Cl. ............... 428/1.1; 252/299.01; 252/299.2; 252/299.61; 252/299.62; 252/299.67; 549/348

(58) Field of Classification Search ............ 252/299.62, 252/299.01, 299.61, 299.67, 299.5, 299.2; 428/1.1; 549/348

See application file for complete search history.

(56) References Cited

U.S. PATENT DOCUMENTS

| | | | |
|---|---|---|---|
| 6,610,216 B2 | 8/2003 | Yumoto et al. | |
| 7,642,035 B2 * | 1/2010 | Shukla et al. | .......... 430/270.11 |
| 2005/0127326 A1 | 6/2005 | Ichihashi | |
| 2007/0229732 A1 * | 10/2007 | Taugerbeck et al. | ........... 349/84 |
| 2008/0281108 A1 * | 11/2008 | Farrand | ....................... 549/348 |

FOREIGN PATENT DOCUMENTS

| | | |
|---|---|---|
| JP | 2002-179669 A | 6/2002 |
| WO | WO 02/34739 A1 | 5/2002 |
| WO | WO 02/34740 A1 | 5/2002 |
| WO | WO 02/100979 A1 | 12/2002 |
| WO | WO 2004/046805 A1 | 6/2004 |

OTHER PUBLICATIONS

Maglioli et al., "Binaphtol systems", "Highly diastereoselective reduction and addition of nucleophiles to binaphthol-protected arylglyoxals", Tet Asymm, 1992, pp. 365-366, vol. 3, No. 3.*
International Search Report completed Dec. 19, 2006 of International Application No. PCT/EP2006/009133 filed Sep. 20, 2006.
Abstract of Chem. Phys. Lett., 1996, 253, (1,2), 141.
M.S. Wong et al., "Synthesis of Novel Non-centrosymmetric Crystalline Materials for 'Quadratic Nonlinear Optics,'" J. Chem. Soc. Chem. Comm., 1994, pp. 249-250.
M.S. Wong et al., "Novel Approach in Molecular Design for Quadratic Nonlinear . . . ," Nonlinear Optic, 1995, vol. 9, pp. 181-186.
L.L. Schafer et al., "Efficient Diastereoselective . . . ," J. Am. Chem. Soc., 2001, vol. 123, pp. 2683-2684.

* cited by examiner

*Primary Examiner*—Shean C Wu
(74) *Attorney, Agent, or Firm*—Millen, White, Zelano & Branigan, P.C.

(57) ABSTRACT

The invention relates to chiral compounds, methods of their preparation, and to their use in optical, electrooptical, electronic, semiconducting or luminescent components or devices, and in decorative, security, cosmetic or diagnostic applications.

26 Claims, No Drawings

CHIRAL COMPOUNDS

FIELD OF THE INVENTION

The invention relates to chiral compounds, methods of their preparation, and to their use in optical, electrooptical, electronic, semiconducting or luminescent components or devices, and in decorative, security, cosmetic or diagnostic applications.

BACKGROUND AND PRIOR ART

Chiral liquid crystal (LC) materials are useful for many applications, for example LC displays (LCD) or polymer films with a twisted structure.

Usually they consist of an LC host material containing one or more chiral dopants which induce the desired helical twist. The effectiveness of a chiral compound to induce a helically twisted molecular structure in a liquid crystal host material is described by its so-called helical twisting power (HTP). The HTP is given in first approximation, which is sufficient for most practical applications, by equation (1):

$$HTP = \frac{1}{p \cdot c} \quad (1)$$

wherein c is the concentration of the chiral compound in the host material and p is the helical pitch.

As can be seen from equation (1), a short pitch can be achieved by using a high amount of the chiral compound or by using a chiral compound with a high absolute value of the HTP. Thus, in case chiral compounds with low HTP are used, high amounts are needed to induce a short pitch. This is disadvantageous, because the chiral compounds known from prior art do often negatively affect the properties of the LC host mixture like the clearing point, dielectric anisotropy, viscosity, driving voltage or switching times, and because chiral compounds can be used only as pure enantiomers and are therefore expensive and difficult to synthesize.

Another disadvantage of prior art chiral compounds is that they often show low solubility in the LC host material, which leads to undesired crystallization at low temperatures. To overcome this disadvantage, typically two or more different chiral dopants have to be added to the host mixture. This implies higher costs and does usually also require additional effort for temperature compensation of the material, as the different dopants have to be selected such that their temperature coefficients of the twist compensate each other.

Consequently, there is a considerable demand for chiral compounds with a high HTP which are easy to synthesize, can be used in low amounts, show low temperature dependence of the twisting power e.g. for utilizing a constant reflection wavelength, show good solubility in an LC host material and do not have a negative influence on the properties of the LC host.

The invention has the aim of providing chiral compounds having these properties, and not having the above-mentioned disadvantages of prior art chiral compounds. Another aim of the invention is to extend the pool of chiral compounds available to the expert. Other aims are immediately evident to the expert from the following description.

The inventors of the present invention have found that these aims can be achieved by providing chiral compounds as claimed in this invention, which comprise a chiral ester comprising a [1,1']binaphthalenyl-2,2'-diol group.

Tetrahedron Asymmetry 1992, 3(3), 365 discloses the use of [1,1']binaphthalenyl-2,2'-diol as a protective group for the diastereoselective preparation of arylglyoxals, however, it does not disclose compounds as claimed in the present invention.

SUMMARY OF THE INVENTION

The invention relates to compounds of formula I

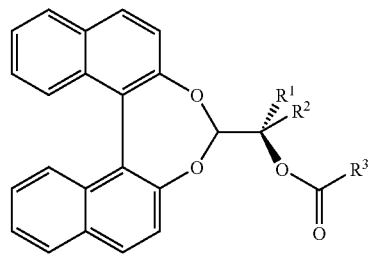

I wherein $R^1$ and $R^2$ are different groups selected from H, halogen, —CN, —NC, —NCO, —NCS, —OCN, —SCN, —C(=O)NR°R°°, —C(=O)Y, —C(=O)R°, —NH$_2$, —NR°R°°, —SH, —SR°, —SO$_3$H, —SO$_2$R°, —OH, —NO$_2$, —CF$_3$, —SF$_5$, optionally substituted silyl, or carbyl or hydrocarbyl with 1 to 40 C atoms that is optionally substituted and optionally comprises one or more hetero atoms, R° and R°° are independently of each other H, straight-chain, branched or cyclic alkyl with 1 to 12 C atoms or aryl with 6 to 12 C atoms, Y is halogen, $R^3$ is carbyl or hydrocarbyl with 1 to 40 C atoms that is optionally substituted and optionally comprises one or more hetero atoms, wherein $R^1$ and $R^2$ are different from —O—CO—$R^3$, and the binaphthyl group is optionally substituted by one or more groups $R^1$ or $R^3$.

The invention further relates to an LC material comprising one or more compounds of formula I.

The invention further relates to a chiral anisotropic polymer obtained by polymerizing a compound of formula I or an LC material as described above and below, preferably in its oriented state in form of a thin film.

The invention further relates to the use of compounds, materials and polymers as described above and below in electrooptical displays, LCDs, optical films, polarizers, compensators, beam splitters, reflective films, alignment layers, colour filters, holographic elements, hot stamping foils, coloured images, decorative or security markings, LC pigments, adhesives, cosmetics, diagnostics, nonlinear optics, optical information storage, electronic devices, organic semiconductors, field effect transistors (FET), components of integrated circuitry (IC), thin film transistors (TFT), Radio Frequency Identification (RFID) tags, organic light emitting diodes (OLED), electroluminescent displays, lighting devices, photovoltaic devices, sensor devices, electrode materials, photoconductors, electrophotographic recording, lasing materials or devices, or as chiral dopants.

Terms and Definitions

The term "film" includes rigid or flexible, self-supporting or free-standing films with mechanical stability, as well as coatings or layers on a supporting substrate or between two substrates.

The term "liquid crystal or mesogenic material" or "liquid crystal or mesogenic compound" means materials or compounds comprising one or more rod- or board-shaped (calamitic) or disc-shaped (discotic) mesogenic groups, i.e. groups with the ability to induce liquid crystal (LC) phase behaviour. The compounds or materials comprising mesogenic groups do not necessarily have to exhibit an LC phase themselves. It is also possible that they show LC phase behaviour only in mixtures with other compounds, or when the mesogenic compounds or materials, or the mixtures thereof, are polymerized.

For the sake of simplicity, the term "liquid crystal material" is used hereinafter for both mesogenic and LC materials.

Polymerizable compounds with one polymerizable group are also referred to as "monoreactive" compounds, compounds with two polymerizable groups as "direactive" compounds, and compounds with more than two polymerizable groups as "multireactive" compounds. Compounds without a polymerizable group are also referred to as "non-reactive" compounds.

The term "reactive mesogen" (RM) means a polymerizable mesogenic or liquid crystal compound.

The binaphthyl group shown in the formulae above and below includes both the S,S- and R,R-isomer.

Above and below, unless stated otherwise, groups like $R^1$, $R^2$ etc., or indices like n etc., in case of multiple occurrence are selected independently from each other, and may be identical or different from each other. Thus, several different groups might be represented by a single label like for example "$R^1$".

The terms 'alkyl', 'aryl' etc. also include multivalent species, for example alkylene, arylene etc.

The term 'carbyl group' denotes any monovalent or multivalent organic radical moiety which comprises at least one carbon atom either without any non-carbon atoms (like for example —C≡C—), or optionally combined with at least one non-carbon atom such as N, O, S, P, Si, Se, As, Te or Ge (for example carbonyl etc.). The term 'hydrocarbyl group' denotes a carbyl group that does additionally contain one or more H atoms and optionally contains one or more hetero atoms like for example N, O, S, P, Si, Se, As, Te or Ge.

DETAILED DESCRIPTION OF THE INVENTION

The compounds of formula I have several advantages
they can easily be synthesized, also on large scale of several hundred grams, with a broad range of derivatives using standard methods that are known from the literature,
the starting materials, S,S-binaphthol or R,R-binaphthol, can be obtained commercially,
they can be prepared enantiomerically pure as compounds of different handedness (left handed and right handed), enabling both left and right handed helices to be formed in a nematic host,
they exhibit a high HTP,
they exhibit a good solubility in LC mixtures,
they are mesogenic or even liquid crystalline,
when used as chiral dopants in an LC host material they do not negatively influence the LC phase of the host.

In formula I $R^1$ and $R^2$ preferably denote P-Sp-X—, or mono- or polynuclear aryl or heteroaryl with 5 to 40 C atoms that is optionally substituted, or denote straight-chain, branched or cyclic alkyl with 1 to 25 C-atoms, which is unsubstituted, mono- or polysubstituted by F, Cl, Br, I or CN, and wherein one or more non-adjacent $CH_2$ groups are optionally replaced, in each case independently from one another, by —O—, —S—, —NH—, —NR$^0$—, —SiR$^0$R$^{00}$—, —CO—, —COO—, —OCO—, —O—CO—O—, —S—CO—, —CO—S—, —CO—NR$^0$—, —NR$^0$—CO—, —NR$^0$—CO—NR$^{00}$—, —CY$^1$=CY$^2$— or —C≡C— in such a manner that O and/or S atoms are not linked directly to one another, wherein $R^0$ and $R^{00}$ are as defined in formula I,
$Y^1$ and $Y^2$ are independently of each other H, F, Cl or CN,
P is a polymerizable group,
Sp is a spacer group or a single bond,
X is —O—, —S—, —CO—, —COO—, —OCO—, —O—COO—, —CO—NR$^0$—, —NR$^0$—CO—, —NR$^0$—CO—NR$^0$—, —OCH$_2$—, —CH$_2$O—, —SCH$_2$—, —CH$_2$S—, —CF$_2$O—, —OCF$_2$—, —CF$_2$S—, —SCF$_2$—, —CF$_2$CH$_2$—, —CH$_2$CF$_2$—, —CF$_2$CF$_2$—, —CH=N—, —N=CH—, —N=N—, —CH=CR$^0$—, —CY$^1$=CY$^2$—, —C≡C—, —CH=CH—COO—, —OCO—CH=CH— or a single bond.

$R^3$ preferably denotes -(Z$^1$-A$^1$)$_m$—R$^4$, wherein
$A^1$ is in case of multiple occurrence independently of one another an aromatic or alicyclic group, which optionally contains one or more hetero atoms selected from N, O and S, and is optionally mono- or polysubstituted by $R^1$,
$Z^1$ is in case of multiple occurrence independently of one another —O—, —S—, —CO—, —COO—, —OCO—, —S—CO—, —CO—S—, —O—COO—, —CO—NR$^0$—, —NR$^0$—CO—, —NR$^0$—CO—NR$^{00}$—, —NR$^0$—CO—O—, —O—CO—NR$^0$—, —OCH$_2$—, —CH$_2$O—, —SCH$_2$—, —CH$_2$S—, —CF$_2$O—, —OCF$_2$—, —CF$_2$S—, —SCF$_2$—, —CH$_2$CH$_2$—, —(CH$_2$)$_4$—, —CF$_2$CH$_2$—, —CH$_2$CF$_2$—, —CF$_2$CF$_2$—, —CH=N—, —N=CH—, —N=N—, —CH=CR$^0$—, —CY$^1$=CY$^2$—, —C≡C—, —CH=CH—COO—, —OCO—CH=CH— or a single bond,
$R^5$ has one of the meanings given for $R^1$,
m is 0, 1, 2, 3 or 4,
and P, Sp, X, $R^0$, $R^{00}$, $Y^1$, $Y^2$ are as defined above.

In another preferred embodiment of the present invention $R^1$ and/or $R^2$ denote an aromatic group, preferably having one of the meanings of $A^1$ given above and below, or denote -(Z$^1$-A$^1$)$_m$—R$^4$ as defined above and below.

Especially preferred are compounds of formula I, wherein
$R^1$ and/or $R^2$ is optionally fluorinated alkyl having 1 to 20, preferably 1 to 12 C atoms,
$R^1$ and/or $R^2$ is optionally substituted aryl having 1 to 12 C atoms, preferably phenyl,
$R^1$ and/or $R^2$ is P-Sp-X—,
the compounds comprise at least one group P-Sp-X—,
the binaphthyl group is substituted, preferably in 6- and/or 6'-position, by $R^1$ or $R^3$ as defined above and below,
$R^4$ is P-Sp_X—,
m is 0,
m is 1 or 2.

Preferred groups $A^1$ are for example furan, pyrrol, thiophene, oxazole, thiazole, thiadiazole, imidazole, phenylene, cyclohexylene, cyclohexenylene, bicyclooctane, pyridine, pyrimidine, pyrazine, azulene, indane, naphthalene, tetrahydronaphthalene, anthracene and phenanthrene, all of which are optionally substituted by one or more groups L,
wherein L is selected from F, Cl, Br, I, —CN, —NO$_2$, —NCO, —NCS, —OCN, —SCN, —C(=O)NR$^0$R$^{00}$, —C(=O)X, —C(=O)R$^0$, —NR$^0$R$^{00}$, —OH, —SF$_5$, wherein R°, R°° and X are as defined above, optionally substituted silyl, aryl with 1 to 12, preferably 1 to 6 C atoms, and straight chain or branched alkyl, alkoxy, alkylcarbonyl, alkoxycarbonyl, alkylcarbonlyoxy or alkoxycarbonyloxy with 1 to 12, preferably 1 to 6 C atoms, wherein one or more H atoms are optionally replaced by F or Cl.

Particularly preferably $A^1$ is selected from 1,4-phenylene, pyridine-2,5-diyl, pyrimidine-2,5-diyl, thiophene-2,5-diyl, naphthalene-2,6-diyl, 1,2,3,4-tetrahydro-naphthalene-2,6-diyl, indane-2,5-diyl, 1,4-cyclohexylene, bicyclo[2.2.2]octane-1,4-diyl, wherein one or two non-adjacent $CH_2$ groups are optionally replaced by O and/or S, wherein these groups are unsubstituted, mono- or polysubstituted by L as defined above.

More preferably L is selected from F, Cl, CN, $NO_2$ or straight chain or branched alkyl, alkoxy, alkylcarbonyl, alkoxycarbonyl, alkylcarbonlyoxy or alkoxycarbonyloxy with 1 to 12 C atoms, wherein the alkyl groups are optionally perfluorinated.

Most preferably L is selected from F, Cl, CN, $NO_2$, $CH_3$, $C_2H_5$, $C(CH_3)_3$, $CH(CH_3)_2$, $CH_2CH(CH_3)C_2H_5$, $OCH_3$, $OC_2H_5$, $COCH_3$, $COC_2H_5$, $COOCH_3$, $COOC_2H_5$, $CF_3$, $OCF_3$, $OCHF_2$ or $OC_2F_5$, in particular F, Cl, CN, $CH_3$, $C_2H_5$, $C(CH_3)_3$, $CH(CH_3)_2$, $OCH_3$, $COCH_3$ or $OCF_3$, most preferably F, Cl, $CH_3$, $C(CH_3)_3$, $OCH_3$ or $COCH_3$.

Some preferred groups -$(Z^1$-$A^1)_m$- are listed below. For reasons of simplicity, Phe in these groups is 1,4-phenylene, PheL is 1,4-phenylene that is substituted with 1 to 4 groups L as defined above, Cyc is 1,4-cyclohexylene and Z has one of the meanings of $Z^1$ given above. The list is comprising the following subformulae as well as their mirror images -PheL-      II-1

-PheL-Z-Phe-      II-2

-PheL-Z-PheL-      II-3

-Phe-Z-Cyc-      II-4

-PheL-Z-Cyc-      II-5

Z is preferably —O—, —COO—, —OCO—, —CH═CH—, —C≡C—, —CH═CH—COO—, —OCO—CH═CH—, —CH₂CH₂— or a single bond.

Very preferably the group -$(Z^1$-$A^1)_m$— is selected from the following formulae and their mirror images

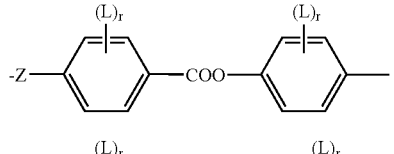
IIa

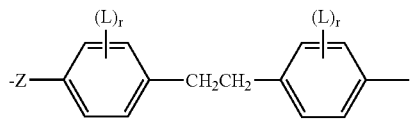
IIb

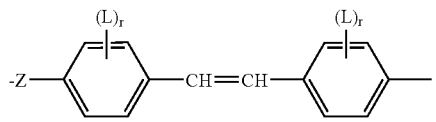
IIc

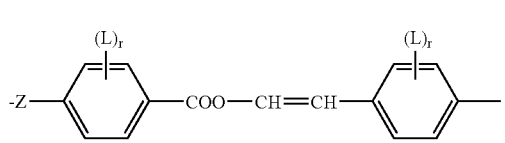
IId

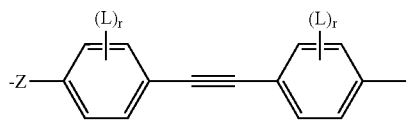
IIe

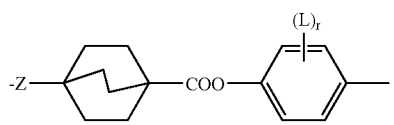
IIf

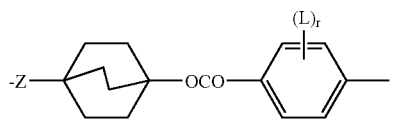
IIg

IIh

IIi

IIk

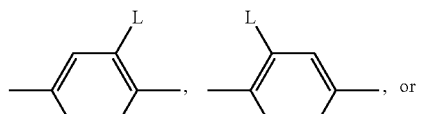

wherein L and Z are as defined above and r is 0, 1, 2, 3 or 4, preferably 0, 1 or 2.

A group

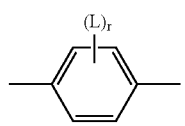

wherein r is different from 0 is preferably denoting

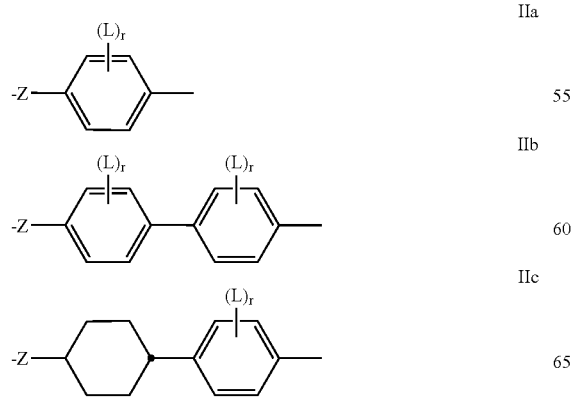

furthermore

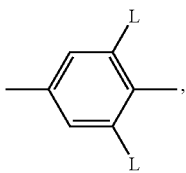

with L having each independently one of the meanings given above.

Especially preferred compounds of formula I comprise at least two groups

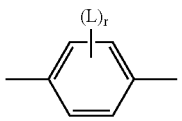

wherein r is 1 and/or at least one group

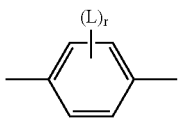

wherein r is 2.

An alkyl or alkoxy radical, i.e. where the terminal $CH_2$ group is replaced by —O—, can be straight-chain or branched. It is preferably straight-chain, has 2, 3, 4, 5, 6, 7 or 8 carbon atoms and accordingly is preferably ethyl, propyl, butyl, pentyl, hexyl, heptyl, octyl, ethoxy, propoxy, butoxy, pentoxy, hexoxy, heptoxy, or octoxy, furthermore methyl, nonyl, decyl, undecyl, dodecyl, tridecyl, tetradecyl, pentadecyl, nonoxy, decoxy, undecoxy, dodecoxy, tridecoxy or tetradecoxy, for example.

Oxaalkyl, i.e. where one $CH_2$ group is replaced by —O—, is preferably straight-chain 2-oxapropyl (=methoxymethyl), 2-(=ethoxymethyl) or 3-oxabutyl (=2-methoxyethyl), 2-, 3-, or 4-oxapentyl, 2-, 3-, 4-, or 5-oxahexyl, 2-, 3-, 4-, 5-, or 6-oxaheptyl, 2-, 3-, 4-, 5-, 6- or 7-oxaoctyl, 2-, 3-, 4-, 5-, 6-, 7- or 8-oxanonyl or 2-, 3-, 4-, 5-, 6-, 7-, 8- or 9-oxadecyl, for example.

An alkyl group wherein one or more $CH_2$ groups are replaced by —CH=CH— can be straight-chain or branched. It is preferably straight-chain, has 2 to 10 C atoms and accordingly is preferably vinyl, prop-1-, or prop-2-enyl, but-1-, 2- or but-3-enyl, pent-1-, 2-, 3- or pent-4-enyl, hex-1-, 2-, 3-, 4- or hex-5-enyl, hept-1-, 2-, 3-, 4-, 5- or hept-6-enyl, oct-1-, 2-, 3-, 4-, 5-, 6- or oct-7-enyl, non-1-, 2-, 3-, 4-, 5-, 6-, 7- or non-8-enyl, dec-1-, 2-, 3-, 4-, 5-, 6-, 7-, 8- or dec-9-enyl.

Especially preferred alkenyl groups are $C_2$-$C_7$-1E-alkenyl, $C_4$-$C_7$-3E-alkenyl, $C_5$-$C_7$-4-alkenyl, $C_6$-$C_7$-5-alkenyl and $C_7$-6-alkenyl, in particular $C_2$-$C_7$-1E-alkenyl, $C_4$-$C_7$-3E-alkenyl and $C_5$-$C_7$-4-alkenyl. Examples for particularly preferred alkenyl groups are vinyl, 1E-propenyl, 1E-butenyl, 1E-pentenyl, 1E-hexenyl, 1E-heptenyl, 3-butenyl, 3E-pentenyl, 3E-hexenyl, 3E-heptenyl, 4-pentenyl, 4Z-hexenyl, 4E-hexenyl, 4Z-heptenyl, 5-hexenyl, 6-heptenyl and the like. Groups having up to 5 C atoms are generally preferred.

In an alkyl group wherein one $CH_2$ group is replaced by —O— and one by —CO—, these radicals are preferably neighbored. Accordingly these radicals together form a carbonyloxy group —CO—O— or an oxycarbonyl group —O—CO—. Preferably this group is straight-chain and has 2 to 6 C atoms. It is accordingly preferably acetyloxy, propionyloxy, butyryloxy, pentanoyloxy, hexanoyloxy, acetyloxymethyl, propionyloxymethyl, butyryloxymethyl, pentanoyloxymethyl, 2-acetyloxyethyl, 2-propionyloxyethyl, 2-butyryloxyethyl, 3-acetyloxypropyl, 3-propionyloxypropyl, 4-acetyloxybutyl, methoxycarbonyl, ethoxycarbonyl, propoxycarbonyl, butoxycarbonyl, pentoxycarbonyl, methoxycarbonylmethyl, ethoxycarbonylmethyl, propoxycarbonylmethyl, butoxycarbonylmethyl, 2-(methoxycarbonyl)ethyl, 2-(ethoxycarbonyl)ethyl, 2-(propoxycarbonyl)ethyl, 3-(methoxycarbonyl)propyl, 3-(ethoxycarbonyl)propyl, 4-(methoxycarbonyl)-butyl.

An alkyl group wherein two or more $CH_2$ groups are replaced by —O— and/or —COO— can be straight-chain or branched. It is preferably straight-chain and has 3 to 12 C atoms. Accordingly it is preferably bis-carboxy-methyl, 2,2-bis-carboxy-ethyl, 3,3-bis-carboxy-propyl, 4,4-bis-carboxy-butyl, 5,5-bis-carboxy-pentyl, 6,6-bis-carboxy-hexyl, 7,7-bis-carboxy-heptyl, 8,8-bis-carboxy-octyl, 9,9-bis-carboxy-nonyl, 10,10-bis-carboxy-decyl, bis-(methoxycarbonyl)-methyl, 2,2-bis-(methoxycarbonyl)-ethyl, 3,3-(methoxycarbonyl)-propyl, 4,4-bis-(methoxycarbonyl)-butyl, 5,5-bis-(methoxycarbonyl)-pentyl, 6,6-bis-(methoxycarbonyl)-hexyl, 7,7-bis-(methoxycarbonyl)-heptyl, 8,8-bis-(methoxycarbonyl)-octyl, bis-(ethoxycarbonyl)-methyl, 2,2-bis-(ethoxycarbonyl)-ethyl, 3,3-bis-(ethoxycarbonyl)-propyl, 4,4-bis-(ethoxycarbonyl)-butyl, 5,5-bis-(ethoxycarbonyl)-hexyl.

An alkyl or alkenyl group that is monosubstituted by CN or $CF_3$ is preferably straight-chain. The substitution by CN or $CF_3$ can be in any desired position.

An alkyl or alkenyl group that is at least monosubstituted by halogen is preferably straight-chain. Halogen is preferably F or Cl, in case of multiple substitution preferably F. The resulting groups include also perfluorinated groups. In case of monosubstitution the F or Cl substituent can be in any desired position, but is preferably in ω-position. Examples for especially preferred straight-chain alkyl groups with a terminal F substituent are fluormethyl, 2-fluorethyl, 3-fluorpropyl, 4-fluorbutyl, 5-fluorpentyl, 6-fluorhexyl and 7-fluorheptyl. Other positions of F are, however, not excluded.

Halogen is preferably F or Cl.

The polymerizable group P is a group that is capable of participating in a polymerization reaction, like radicalic or ionic chain polymerization, polyaddition or polycondensation, or capable of being grafted, for example by condensation or addition, to a polymer backbone in a polymeranaloguous reaction. Especially preferred are polymerizable groups for chain polymerization reactions, like radicalic, cationic or anionic polymerization. Very preferred are polymerizable groups comprising a C—C double or triple bond, and polymerizable groups capable of polymerization by a ring-opening reaction, like oxetanes or epoxides.

Very preferably the polymerizable group P is selected from $CH_2=CW^1$—

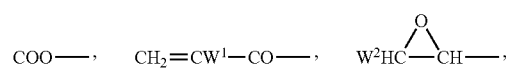

-continued

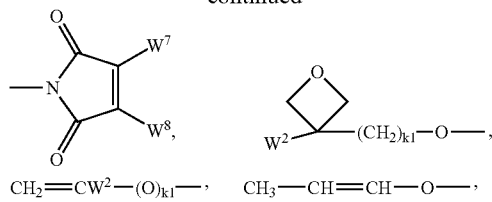

$(CH_2=CH)_2CH-OCO-$, $(CH_2=CH-CH_2)_2CH-OCO-$, $(CH_2=CH)_2CH-O-$, $(CH_2=CH-CH_2)_2N-$, $(CH_2=CH-CH_2)_2N-CO-$, $HO-CW^2W^3-$, $HS-CW^2W^3-$, $HW^2N-$, $HO-CW^2W^3-NH-$, $CH_2=CW^1-CO-NH-$, $CH_2=CH-(COO)_{k1}$-Phe-$(O)_{k2}-$, $CH_2=CH-(CO)_{k1}$-Phe-$(O)_{k2}-$, Phe-$CH=CH-$, $HOOC-$, $OCN-$, and $W^4W^5W^6Si-$, with $W^1$ being H, F, Cl, CN, $CF_3$, phenyl or alkyl with 1 to 5 C-atoms, in particular H, $C_1$ or $CH_3$, $W^2$ and $W^3$ being independently of each other H or alkyl with 1 to 5 C-atoms, in particular H, methyl, ethyl or n-propyl, $W^4$, $W^5$ and $W^6$ being independently of each other Cl, oxaalkyl or oxacarbonylalkyl with 1 to 5 C-atoms, $W^7$ and $W^8$ being independently of each other H, Cl or alkyl with 1 to 5 C-atoms, Phe being 1,4-phenylene that is optionally substituted by one or more groups L as defined above, and $k_1$ and $k_2$ being independently of each other 0 or 1.

Especially preferred groups P are $CH_2=CH-COO-$, $CH_2=C(CH_3)-COO-$, $CH_2=CH-$, $CH_2=CH-O-$, $(CH_2=CH)_2CH-OCO-$, $(CH_2=CH)_2CH-O-$,

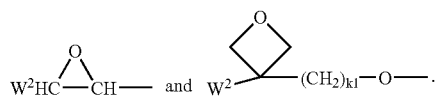

Especially preferably Pg is a vinyl group, an acrylate group, a methacrylate group, an oxetane group or an epoxy group, especially preferably an acrylate or methacrylate group.

Very preferred are acrylate and oxetane groups. Oxetanes produce less shrinkage upon polymerization (cross-linking), which results in less stress development within films, leading to higher retention of ordering and fewer defects. Oxetane cross-linking also requires a cationic initiator, which unlike free radical initiator is inert to oxygen.

As spacer group all groups can be used that are known for this purpose to the skilled in the art. The spacer group Sp is preferably alkylene with 1 to 20 C atoms, preferably 1 to 12 C-atoms, which is optionally mono- or polysubstituted by F, Cl, Br, I or CN, and wherein one or more non-adjacent $CH_2$ groups are optionally replaced, in each case independently from one another, by $-O-$, $-S-$, $-NH-$, $-NR^0-$, $-SiR^0R^{00}-$, $-CO-$, $-COO-$, $-OCO-$, $-OCO-O-$, $-S-CO-$, $-CO-S-$, $-NR^0-CO-O-$, $-O-CO-NR^0-$, $-NR^0-CO-NR^0-$, $-CH=CH-$ or $-C\equiv C-$ in such a manner that O and/or S atoms are not linked directly to one another.

Typical groups Sp are, for example, $-(CH_2)_p-$, $-(CH_2CH_2O)_q-CH_2CH_2-$, $-CH_2CH_2-S-CH_2CH_2-$ or $-CH_2CH_2-NH-CH_2CH_2-$ or $-(SiR^0R^{00}-O)_p-$, with p being an integer from 2 to 12, q being an integer from 1 to 3 and $R^0$ and $R^{00}$ having the meanings given above.

Preferred groups Sp are ethylene, propylene, butylene, pentylene, hexylene, heptylene, octylene, nonylene, decylene, undecylene, dodecylene, octadecylene, ethyleneoxyethylene, methyleneoxybutylene, ethylene-thioethylene, ethylene-N-methyl-iminoethylene, 1-methylalkylene, ethenylene, propenylene and butenylene for example.

Further preferred are compounds with one or two groups P-Sp-X wherein Sp is a single bond. In case of compounds with two groups P-Sp-X, each of the two polymerizable groups P and the two spacer groups Sp can be identical or different.

Particularly preferred compounds of formula I are those of the following formulae Ia
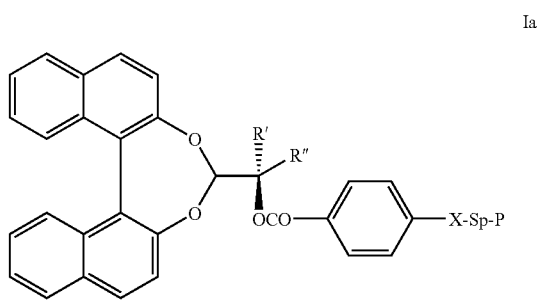

Ib
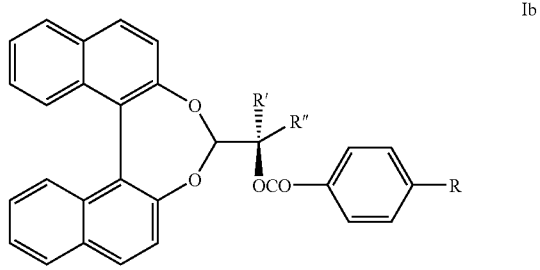

Ic
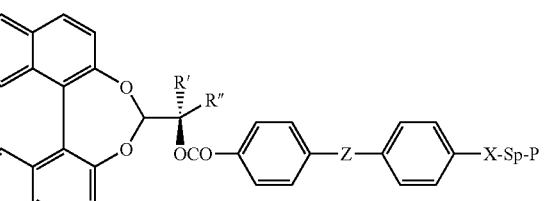

Id
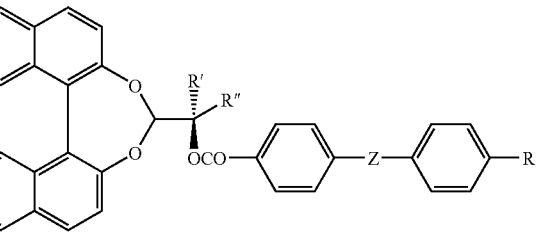

Ie
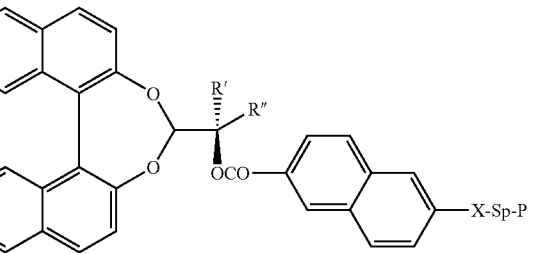

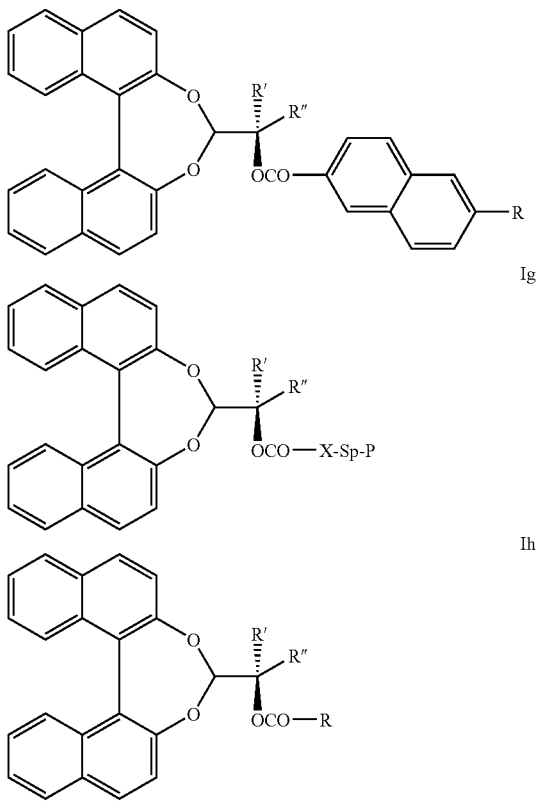

wherein P, Sp and X are as defined above, and the binaphthyl, naphthyl and phenyl groups are optionally substituted by one or more groups L as defined above, R' and R" are different groups selected from optionally fluorinated alkyl having 1 to 20, preferably 1 to 12 C atoms, and aryl having 1 to 12 C atoms, preferably phenyl, that is optionally substituted, Z is as defined above, and is preferably OCO, COO, $OCF_2$, $CF_2O$, or a single bond, R is optionally fluorinated alkyl or alkoxy with 1 to 12, preferably 1 to 8 C atoms, or alkenyl with 2 to 7 C atoms.

Especially are compounds of the above preferred formulae wherein

—R' and R" are selected from phenyl, 4-fluorophenyl, methyl, ethyl, n-propyl, i-propyl, t-butyl, n-pentyl and trifluoromethyl, R' is methyl and R" is phenyl, or vice versa, one of R' and R" is t-butyl and the other is methyl or phenyl, one of R' and R" is phenyl and the other is 4-fluorophenyl, ethyl, n-propyl or trifluoromethyl, —X-Sp-P is —O—$(CH_2)_n$—P', wherein P' is acrylate or methacrylate and n is 2, 3, 4, 5, 6, 7 or 8, preferably 3 or 6.

Especially preferred are compounds of the following sub-formulae, including the mirror images of the [1,1']binaphthalenyl-2,2'-diol group not shown.

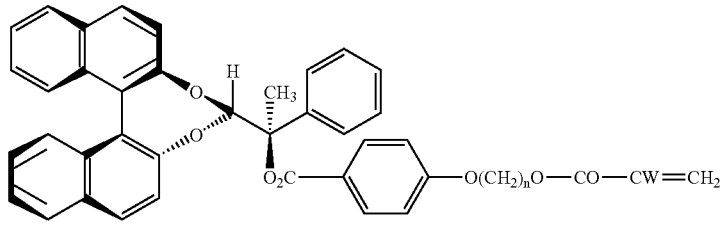

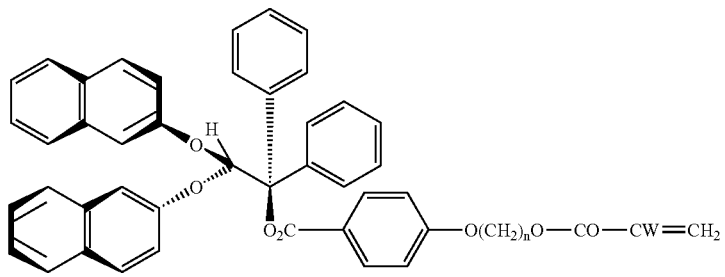

-continued
Ia3
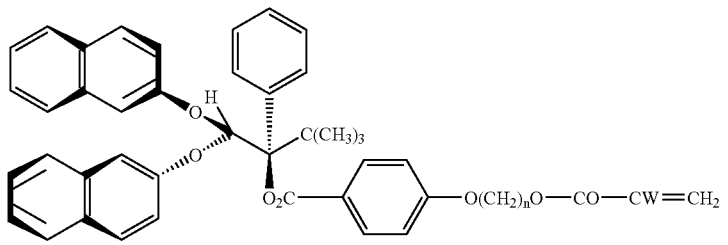
Ia4
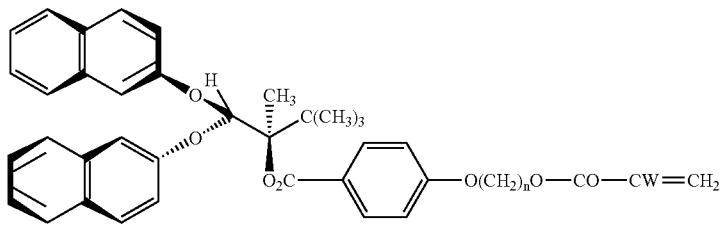
Ia5
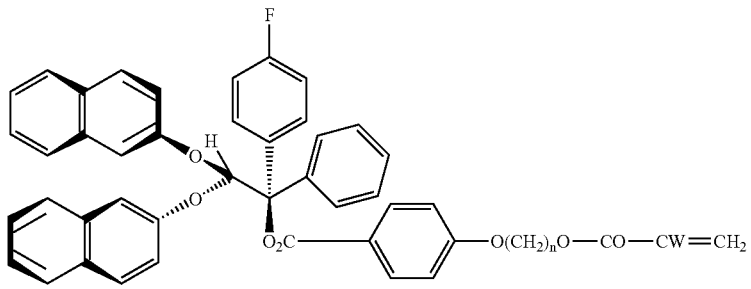
Ia6
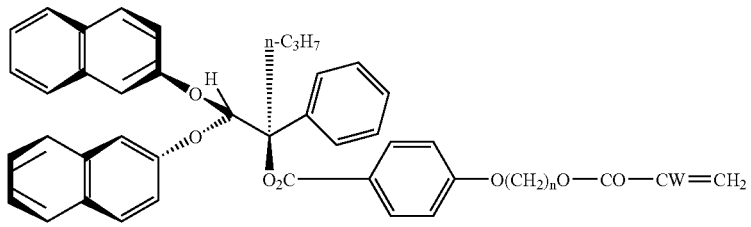
Ia7
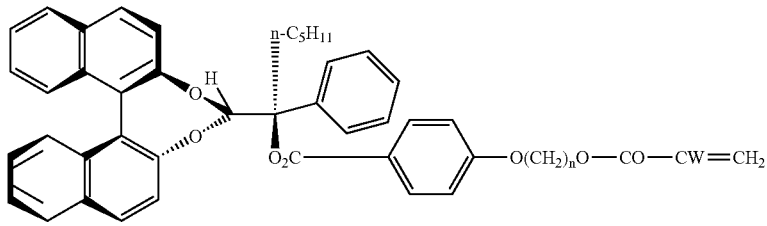
Ia8
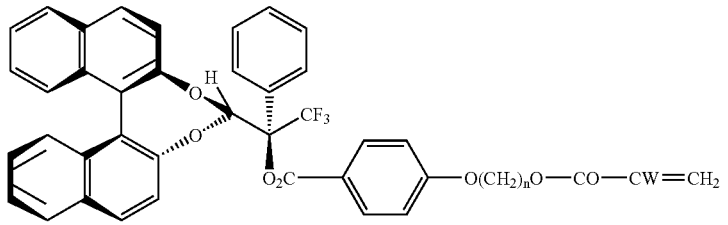

-continued
Ib1
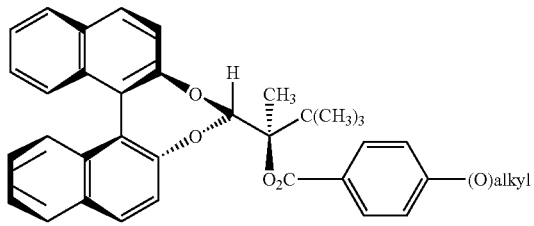
Ic1
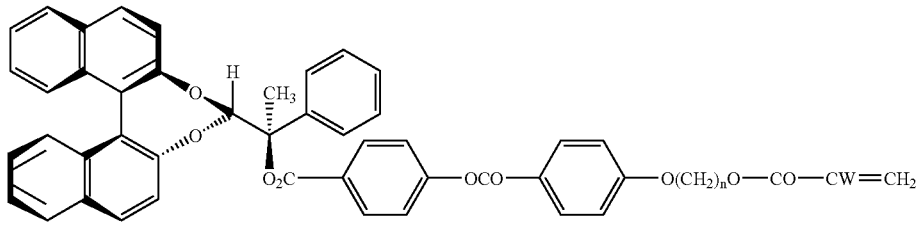
Id1
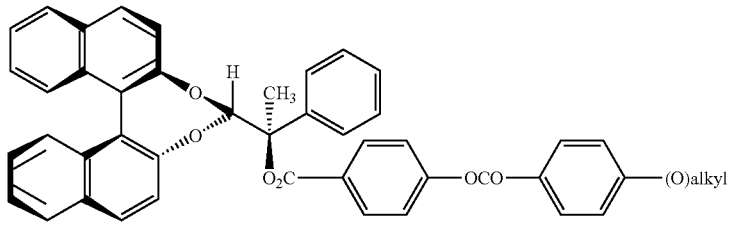
Id2
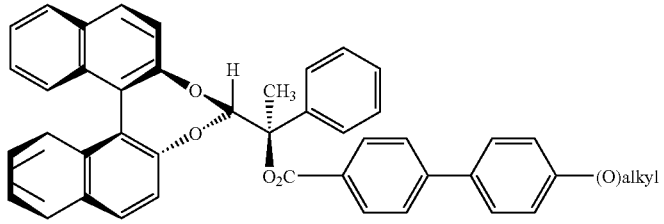
Ie1
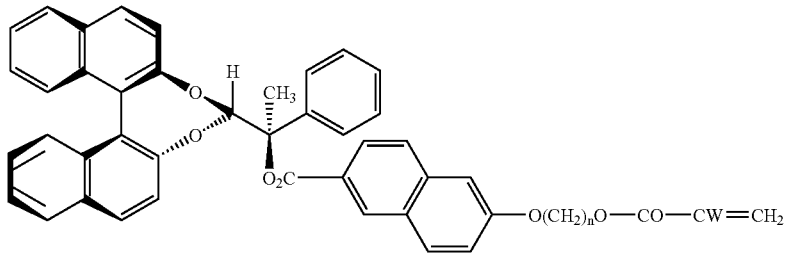
Ig1
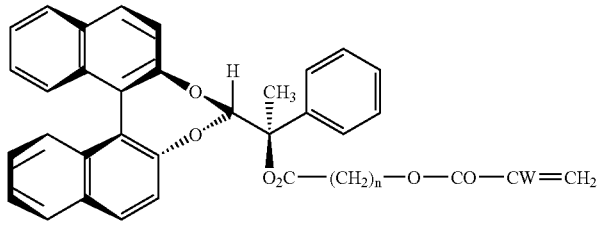

wherein the binaphthyl, naphthyl and phenyl groups are optionally substituted by one or more groups L as defined above, W is H or $CH_3$, n is 2, 3, 4, 5 or 6, preferably 3 or 6, (O)alkyl is alkyl or alkoxy with 1 to 12, preferably 1, 2, 3, 4, 5 or 6 C atoms.

The compounds of formula I can be synthesized according to or in analogy to methods which are known per se and which are described in the literature and in standard works of organic chemistry such as, for example, Houben-Weyl, Methoden der organischen Chemie, Thieme-Verlag, Stuttgart. Preferably the compounds are synthesized according or in analogy to reaction scheme 1 below. Further methods of preparation are shown in the examples.

According to a preferred method, sodium salt of binaphthol is reacted with a dibromoacetophenone moiety to form a ketone which undergoes a reaction with an alkyl Grignard reagent to form a hydroxyl intermediate. The OH group is esterified by an appropriate acid in the presence of dicyclohexylcarbodiimide and dimethylaminopyridine or by an acid chloride in the presence of a base, preferably triethylamine, to give a desired chiral product. This is depicted in Scheme 1.

The method to prepare a compound of formula I is another aspect of the invention.

comprising a chiral LC medium operating in the isotropic or blue phase as described in WO 02/93244.

The inventive compounds of formula I are also suitable for use in thermochromic or photochromic LC media, which change their colour upon temperature change or photoirradiation, respectively.

Thus, another aspect of the invention is an LC mixture comprising at least one chiral compound of formula I. Yet another aspect of the invention are cholesteric LCDs comprising cholesteric LC media containing at least one chiral compound of formula I.

The compounds of formula I have a good solubility in LC host mixtures, and can be added as dopants to LC hosts in high amounts without significantly affecting the phase behaviour and electrooptical properties of the mixture. Undesired spontaneous crystallization at low temperatures is thereby reduced and the operating temperature range of the mixture can be broadened. Furthermore, they can be used for the preparation of highly twisted LC media even if they have a low HTP, because the dopant concentration can be increased to yield low pitch values (i.e. high twist) without affecting the mixture properties. The use of a second dopant, which is often added to avoid crystallization, can thus be avoided. As the chiral compounds of formula I exhibit high HTP values, an LC mixture with high helical twist, i.e. a low pitch, can be prepared by adding these compounds in very small amounts.

Scheme 1:

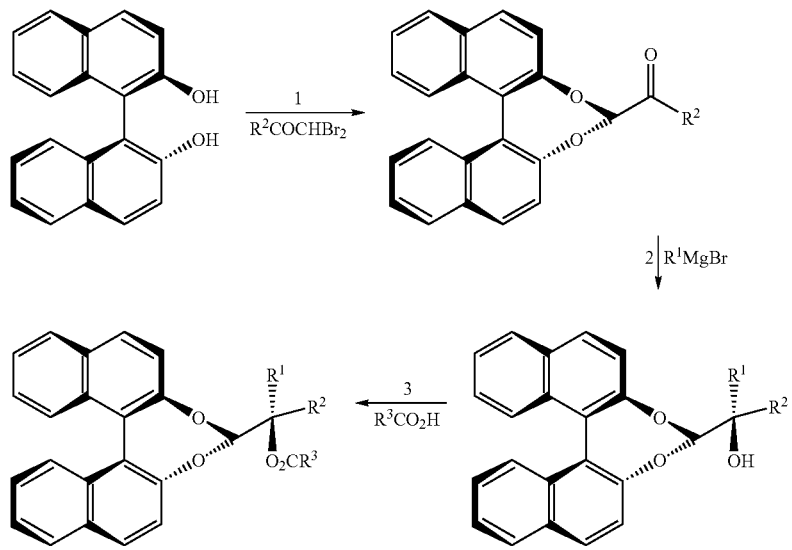

(wherein $R^1$, $R^2$ and $R^3$ are as defined above)

The compounds of formula I can be used in LC mixtures for LCDs exhibiting a twisted structure like, for example, twisted or supertwisted nematic (TN, STN) displays with multiplex or active matrix addressing, or in cholesteic displays like surface stabilized or polymer stabilized cholesteric texture displays (SSCT, PSCT) as described in WO 92/19695, WO 93/23496, U.S. Pat. No. 5,453,863 or U.S. Pat. No. 5,493,430, for LCDs with variable pitch, like multi-domain LCDs as described in WO 98/57223, multicolour cholesteric displays as described in U.S. Pat. No. 5,668,614, or displays Such an LC mixture comprises preferably 0.1 to 30%, in particular 1 to 25% and very particularly preferably 2 to 15% by weight of chiral compounds of formula I. Preferably it comprises 1 to 3 chiral compounds of formula I.

In a preferred embodiment of the invention the LC mixture is consisting of 2 to 25, preferably 3 to 15 compounds, at least one of which is a chiral compound of formula I. The other compounds are preferably low molecular weight LC compounds selected from nematic or nematogenic substances, for example from the known classes of the azoxybenzenes, benzylidene-anilines, biphenyls, terphenyls, phenyl or cyclohexyl benzoates, phenyl or cyclohexyl esters of cyclohexanecarboxylic acid, phenyl or cyclohexyl esters of cyclohexylbenzoic acid, phenyl or cyclohexyl esters of cyclohexylcyclohexanecarboxylic acid, cyclohexylphenyl esters of benzoic acid, of cyclohexanecarboxylic acid and of cyclohexylcyclohexanecarboxylic acid, phenylcyclohexanes, cyclohexylbiphenyls, phenylcyclohexylcyclohexanes, cyclohexylcyclohexanes, cyclohexylcyclohexenes, cyclohexylcyclohexylcyclohexenes, 1,4-bis-cyclohexylbenzenes, 4,4'-bis-cyclohexylbiphenyls, phenyl- or cyclohexylpyrimidines, phenyl- or cyclohexylpyridines, phenyl- or cyclohexylpyridazines, phenyl- or cyclohexyldioxanes, phenyl- or cyclohexyl-1,3-dithianes, 1,2-diphenyl-ethanes, 1,2-dicyclohexylethanes, 1-phenyl-2-cyclohexylethanes, 1-cyclohexyl-2-(4-phenylcyclohexyl)ethanes, 1-cyclohexyl-2-biphenyl-ethanes, 1-phenyl-2-cyclohexylphenylethanes, optionally halogenated stilbenes, benzyl phenyl ether, tolanes, substituted cinnamic acids and further classes of nematic or nematogenic substances. The 1,4-phenylene groups in these compounds may also be laterally mono- or difluorinated. The LC mixture is preferably based on achiral compounds of this type.

The most important compounds that can be used as components of the LC mixture can be characterized by the following formula

R'-L'-G'-E-R"

wherein L' and E, which may be identical or different, are in each case, independently from one another, a bivalent radical from the group formed by -Phe-, -Cyc-, -Phe-Phe-, -Phe-Cyc-, -Cyc-Cyc-, -Pyr-, -Dio-, —B-Phe- and —B-Cyc- and their mirror images, where Phe is unsubstituted or fluorine-substituted 1,4-phenylene, Cyc is trans-1,4-cyclohexylene or 1,4-cyclohexenylene, Pyr is pyrimidine-2,5-diyl or pyridine-2,5-diyl, Dio is 1,3-dioxane-2,5-diyl abd B is 2-(trans-1,4-cyclohexyl)ethyl, pyrimidine-2,5-diyl, pyridine-2,5-diyl or 1,3-dioxane-2,5-diyl.

G' in these compounds is selected from the following bivalent groups —CH=CH—, —N(O)N—, —CH=CY—, —CH=N(O)—, —C≡C—, —CH$_2$—CH$_2$-, —CO—O—, —CH$_2$—O—, —CO—S—, —CH$_2$—S—, —CH=N—, —COO-Phe-COO— or a single bond, with Y being halogen, preferably chlorine, or —CN.

R' and R" are, in each case, independently of one another, alkyl, alkenyl, alkoxy, alkenyloxy, alkanoyloxy, alkoxycarbonyl or alkoxycarbonyloxy with 1 to 18, preferably 3 to 12 C atoms, or alternatively one of R' and R" is F, CF$_3$, OCF$_3$, Cl, NCS or CN.

In most of these compounds R' and R" are, in each case, independently of each another, alkyl, alkenyl or alkoxy with different chain length, wherein the sum of C atoms in nematic media generally is between 2 and 9, preferably between 2 and 7.

Many of these compounds or mixtures thereof are commercially available. All of these compounds are either known or can be prepared by methods which are known per se, as described in the literature (for example in the standard works such as Houben-Weyl, Methoden der Organischen Chemie [Methods of Organic Chemistry], George-Thieme-Verlag, Stuttgart), to be precise under reaction conditions which are known and suitable for said reactions. Use may also be made here of variants which are known per se, but are not mentioned here.

A preferred use of the compounds of formula I is the preparation of polymerizable LC mixtures, anisotropic polymer gels and anisotropic polymer films, in particular polymer films that exhibit a helically twisted molecular structure with uniform planar orientation, i.e. wherein the helical axis is oriented perpendicular to the plane of the film, like oriented cholesteric films.

Anisotropic polymer gels and displays comprising them are disclosed for example in DE 195 04 224 and GB 2 279 659.

Oriented cholesteric polymer films can be used for example as broadband reflective polarizers, colour filters, security markings, or for the preparation of LC pigments.

Thus, another aspect of the invention is a polymerizable LC material comprising one or more compounds of formula I and one or more further compounds, which can also be polymerizable and/or LC compounds.

The polymerizable LC material is preferably a mixture of two or more compounds, at least one of which is polymerizable or crosslinkable compound. Polymerizable compounds with one polymerizable group are hereinafter also referred to as "monoreactive". Crosslinkable compounds, i.e. having two or more polymerizable groups, are hereinafter also referred to as "di- or multireactive".

The polymerizable mesogenic or LC compounds are preferably monomers, very preferably calamitic monomers. These materials typically have good optical properties, like reduced chromaticity, and can be easily and quickly aligned into the desired orientation, which is especially important for the industrial production of polymer films at large scale. It is also possible that the polymerizable material comprises one or more discotic monomers.

The polymerizable materials as described above and below are another aspect of the invention.

Polymerizable mesogenic mono-, di- and multireactive compounds suitable for the present invention can be prepared by methods which are known per se and which are described in standard works of organic chemistry like for example Houben-Weyl, Methoden der organischen Chemie, Thieme-Verlag, Stuttgart.

Suitable polymerizable mesogenic or LC compounds for use as monomer or comonomer in a polymerizable LC mixture are disclosed for example in WO 93/22397, EP 0 261 712, DE 195 04 224, WO 95/22586, WO 97/00600, U.S. Pat. No. 5,518,652, U.S. Pat. No. 5,750,051, U.S. Pat. No. 5,770,107 and U.S. Pat. No. 6,514,578.

Examples of suitable and preferred polymerizable mesogenic or LC compounds (reactive mesogens) are shown in the following list.

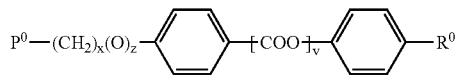
(R1)

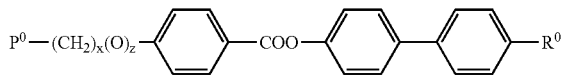
(R2)

-continued
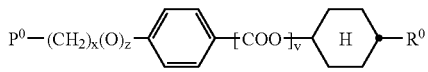 (R3)
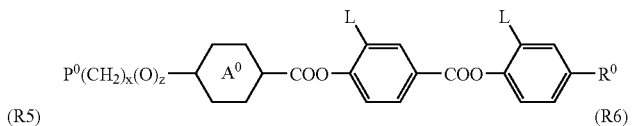 (R4)
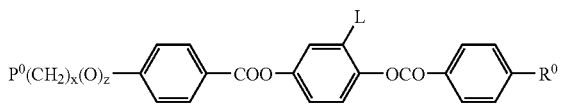 (R5)
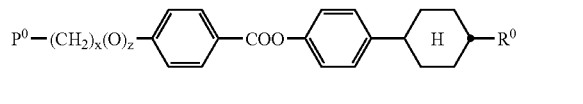 (R6)
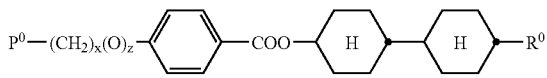 (R7)
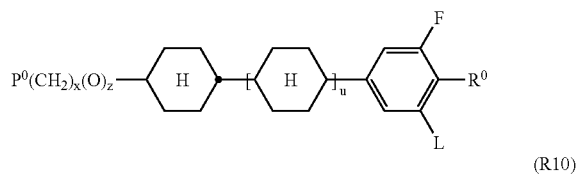 (R8)
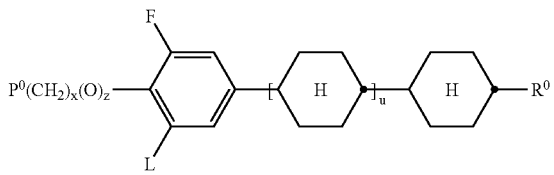 (R9)
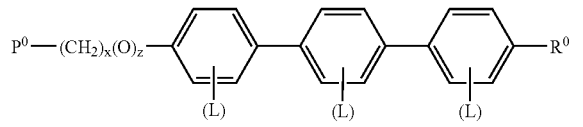 (R10)
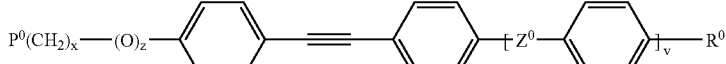 (R11)
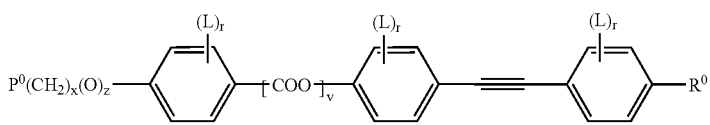 (R12)
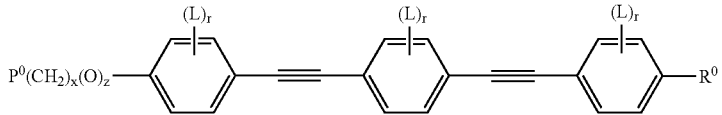 (R13)
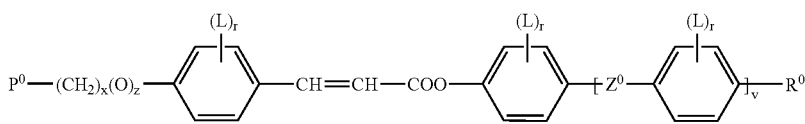 (R14)
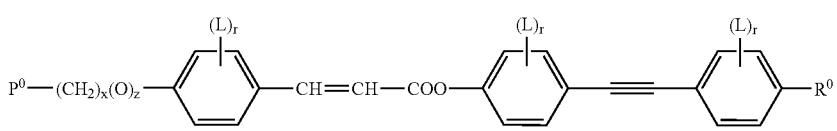 (R15)
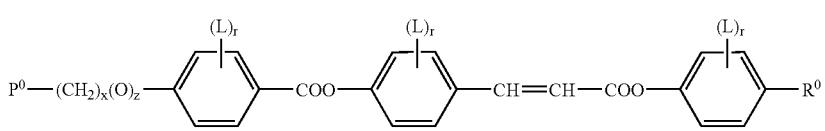 (R16)
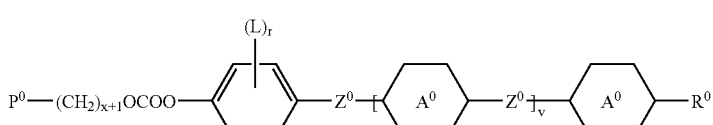 (R17)
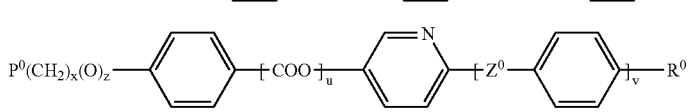 (R18)

-continued
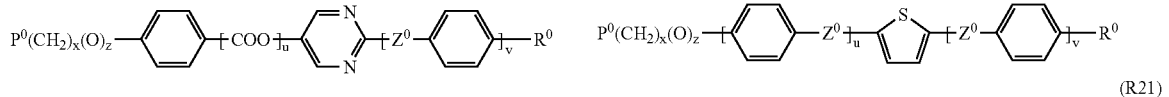
(R19)
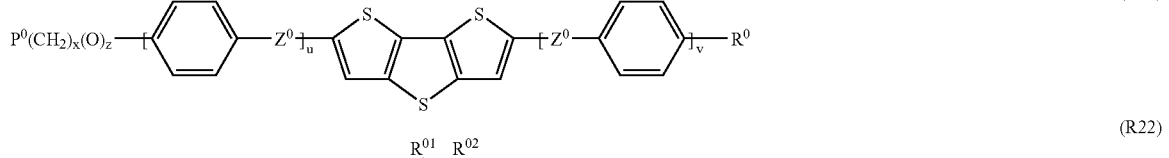
(R20)
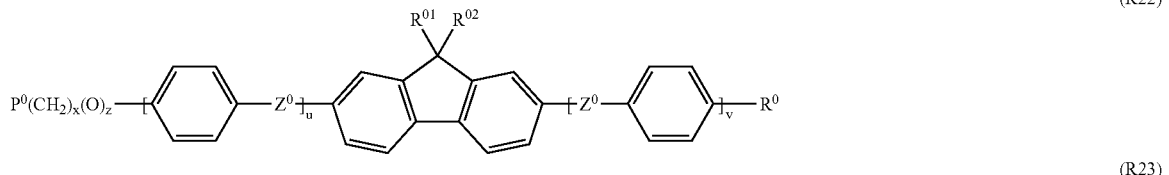
(R21)
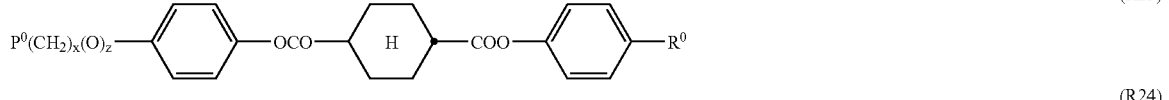
(R22)
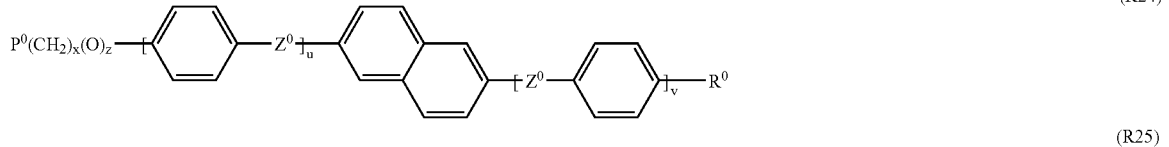
(R23)
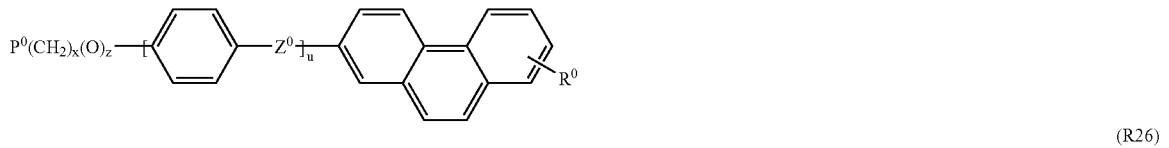
(R24)
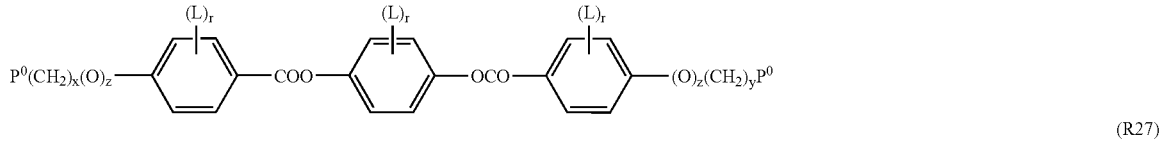
(R25)
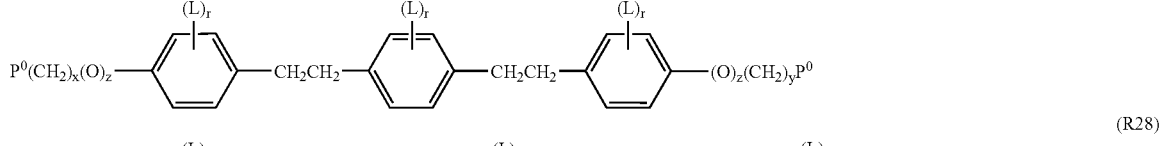
(R26)
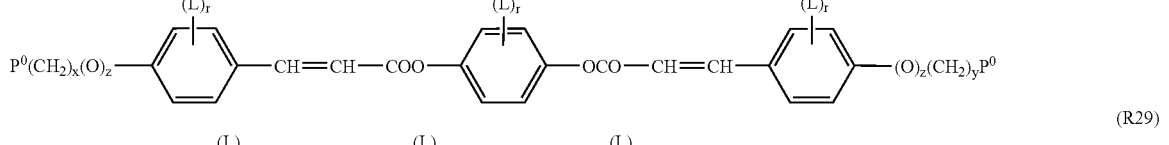
(R27)
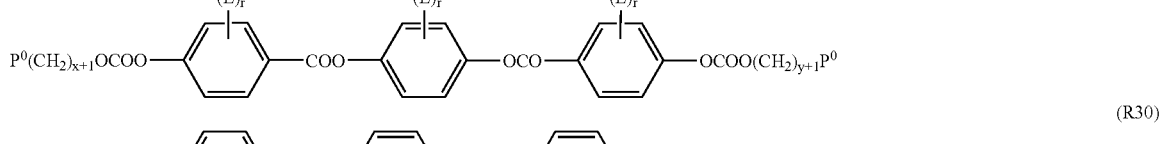
(R28)
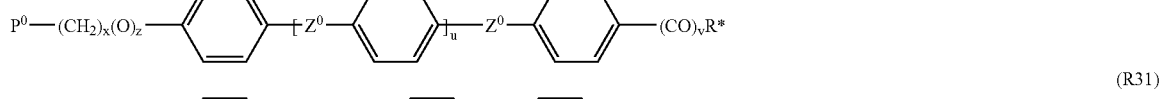
(R29)
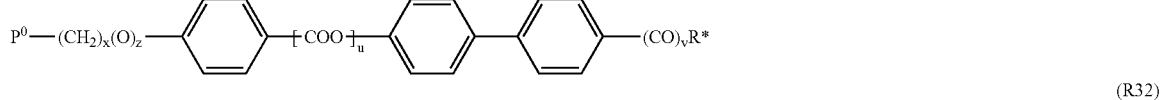
(R30)
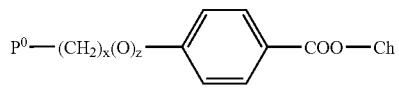
(R31)

-continued

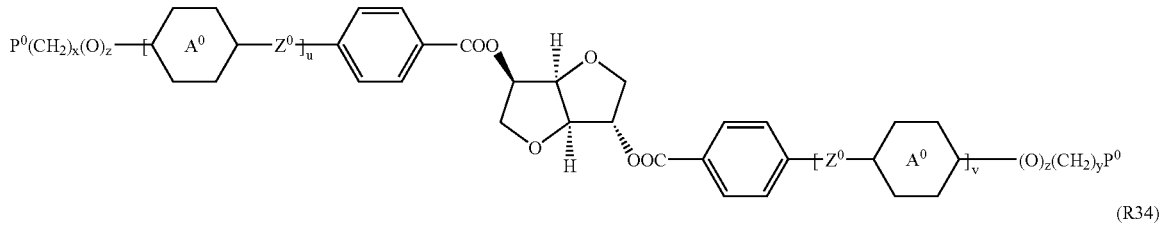

(R33)

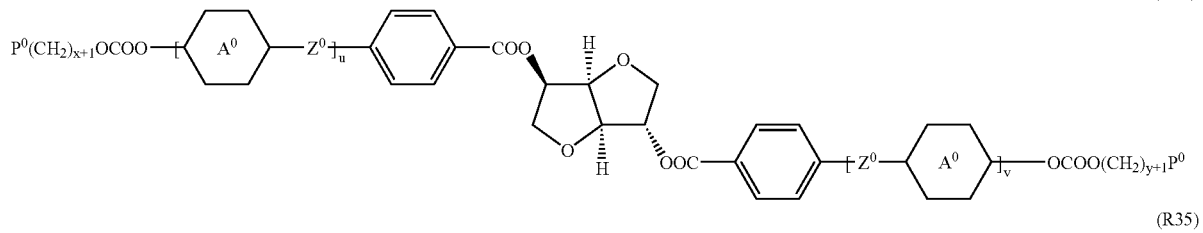

(R34)

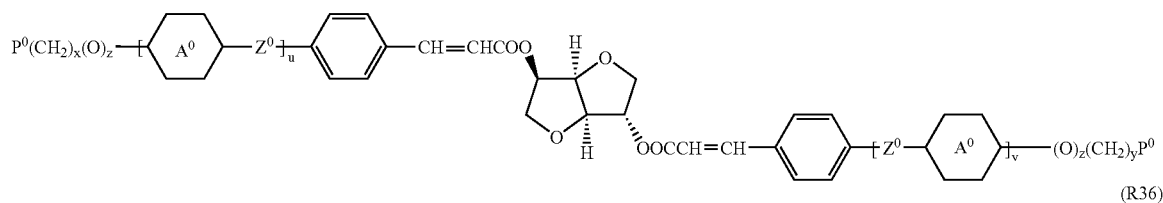

(R35)

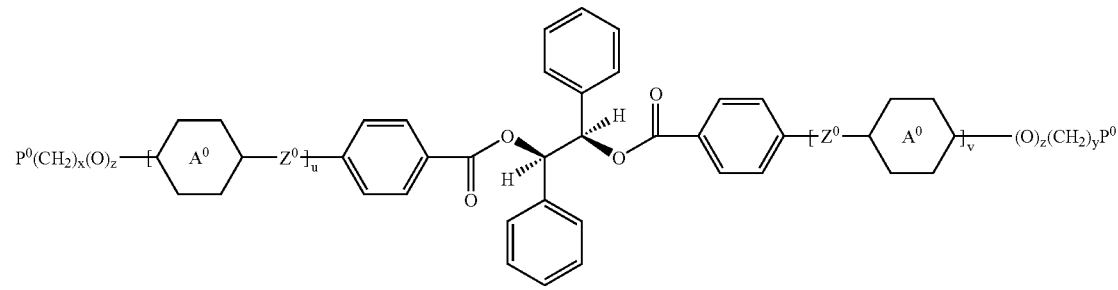

(R36)

wherein
P⁰ is, in case of multiple occurrence independently of one another, a polymerizable group, preferably an acryl, methacryl, oxetane, epoxy, vinyl, vinyloxy, propenyl ether or styrene group,
r is 0, 1, 2, 3 or 4,
x and y are independently of each other 0 or identical or different integers from 1 to 12,
z is 0 or 1, with z being 0 if the adjacent x or y is 0,
A⁰ is, in case of multiple occurrence independently of one another, 1,4-phenylene that is optionally substituted with 1, 2, 3 or 4 groups L, or trans-1,4-cyclohexylene,
u and v are independently of each other 0 or 1,
Z⁰ is, in case of multiple occurrence independently of one another, —COO—, —OCO—, —CH$_2$CH$_2$—, —C≡C—, —CH=CH—, —CH=CH—COO—, —OCO—CH=CH— or a single bond,
R⁰ is alkyl, alkoxy, thioalkyl, alkylcarbonyl, alkoxycarbonyl, alkylcarbonyloxy or alkoxycarbonyloxy with 1 or more, preferably 1 to 15 C atoms which is optionally fluorinated, or is Y⁰ or P—(CH$_2$)$_y$—(O)$_z$—,
Y⁰ is F, Cl, CN, NO$_2$, OCH$_3$, OCN, SCN, SF$_5$, optionally fluorinated alkylcarbonyl, alkoxycarbonyl, alkylcarbonyloxy or alkoxycarbonyloxy with 1 to 4 C atoms, or mono- oligo- or polyfluorinated alkyl or alkoxy with 1 to 4 C atoms,
R$^{01,02}$ are independently of each other H, R⁰ or Y⁰,
R* is a chiral alkyl or alkoxy group with 4 or more, preferably 4 to 12 C atoms, like 2-methylbutyl, 2-methyloctyl, 2-methylbutoxy or 2-methyloctoxy,
Ch is a chiral group selected from cholesteryl, estradiol, or terpenoid radicals like menthyl or citronellyl,
L is, in case of multiple occurrence independently of one another, H, F, Cl, CN or optionally halogenated alkyl, alkoxy, alkylcarbonyl, alkoxycarbonyl, alkylcarbonyloxy or alkoxycarbonyloxy with 1 to 5 C atoms,
and wherein the benzene rings can additionally be substituted with one or more identical or different groups L.

In addition to compounds of formula I, the polymerizable material may further comprise one or more polymerizable or unpolymerizable chiral compounds.

Suitable unpolymerizable chiral compounds are for example standard chiral dopants like R- or S-811, R- or S-1011, R- or S-2011, R- or S-3011, R- or S-4011, R- or S-5011, or CB 15 (all available from Merck KGaA, Darmstadt, Germany), sorbitols as described in WO 98/00428, hydrobenzoins as described in GB 2,328,207, chiral binaphthols as described in WO 02/94805, chiral binaphthol acetals as described in WO 02/34739, chiral TADDOLs as described in WO 02/06265, or chiral compounds having fluorinated linkage groups as described in WO 02/06196 or WO 02/06195. Suitable polymerizable chiral compounds are for example those listed above, or the polymerizable chiral material Paliocolor® LC756 (from BASF AG, Ludwigshafen, Germany).

The general preparation of polymer LC films according to this invention is known to the ordinary expert and described in the literature. Typically a polymerizable LC material is coated or otherwise applied onto a substrate where it aligns into uniform orientation, and polymerized in situ in its LC phase at a selected temperature for example by exposure to heat or actinic radiation, preferably by photo-polymerization, very preferably by UV-photopolymerization, to fix the alignment of the LC molecules. If necessary, uniform alignment can promoted by additional means like shearing or annealing the LC material, surface treatment of the substrate, or adding surfactants to the LC material.

As substrate for example glass or quartz sheets or plastic films can be used. It is also possible to put a second substrate on top of the coated material prior to and/or during and/or after polymerization. The substrates can be removed after polymerization or not. When using two substrates in case of curing by actinic radiation, at least one substrate has to be transmissive for the actinic radiation used for the polymerisation. Isotropic or birefringent substrates can be used. In case the substrate is not removed from the polymerized film after polymerisation, preferably isotropic substrates are used.

Suitable and preferred plastic substrates are for example films of polyester such as polyethyleneterephthalate (PET) or polyethylenenaphthalate (PEN), polyvinylalcohol (PVA), polycarbonate (PC) or triacetylcellulose (TAC), very preferably PET or TAC films. As birefringent substrates for example uniaxially stretched plastics film can be used. PET films are commercially available for example from DuPont Teijin Films under the trade name Melinex®.

The polymerizable material can be applied onto the substrate by conventional coating techniques like spin-coating or blade coating. It can also be applied to the substrate by conventional printing techniques which are known to the expert, like for example screen printing, offset printing, reel-to-reel printing, letter press printing, gravure printing, rotogravure printing, flexographic printing, intaglio printing, pad printing, heat-seal printing, ink-jet printing or printing by means of a stamp or printing plate.

It is also possible to dissolve the polymerizable material in a suitable solvent. This solution is then coated or printed onto the substrate, for example by spin-coating or printing or other known techniques, and the solvent is evaporated off before polymerization. In many cases it is suitable to heat the mixture in order to facilitate the evaporation of the solvent. As solvents for example standard organic solvents can be used. The solvents can be selected for example from ketones such as acetone, methyl ethyl ketone, methyl propyl ketone or cyclohexanone; acetates such as methyl, ethyl or butyl acetate or methyl acetoacetate; alcohols such as methanol, ethanol or isopropyl alcohol; aromatic solvents such as toluene or xylene; halogenated hydrocarbons such as di- or trichloromethane; glycols or their esters such as PGMEA (propyl glycol monomethyl ether acetate), 7-butyrolactone, and the like. It is also possible to use binary, ternary or higher mixtures of the above solvents.

Initial alignment (e.g. planar alignment) of the polymerizable LC material can be achieved for example by rubbing treatment of the substrate, by shearing the material during or after coating, by annealing the material before polymerization, by application of an alignment layer, by applying a magnetic or electric field to the coated material, or by the addition of surface-active compounds to the material. Reviews of alignment techniques are given for example by 1. Sage in "Thermotropic Liquid Crystals", edited by G. W. Gray, John Wiley & Sons, 1987, pages 75-77; and by T. Uchida and H. Seki in "Liquid Crystals—Applications and Uses Vol. 3", edited by B. Bahadur, World Scientific Publishing, Singapore 1992, pages 1-63. A review of alignment materials and techniques is given by J. Cognard, Mol. Cryst. Liq. Cryst. 78, Supplement 1 (1981), pages 1-77.

Especially preferred is a polymerizable material comprising one or more surfactants that promote a specific surface alignment of the LC molecules. Suitable surfactants are described for example in J. Cognard, Mol. Cryst. Liq. Cryst. 78, Supplement 1, 1-77 (1981). Preferred aligning agents for planar alignment are for example non-ionic surfactants, preferably fluorocarbon surfactants such as the commercially available Fluorad FC-171®g (from 3M Co.) or Zonyl FSN® (from DuPont), multiblock surfactants as described in GB 2 383 040 or polymerizable surfactants as described in EP 1 256 617.

It is also possible to apply an alignment layer onto the substrate and provide the polymerizable material onto this alignment layer. Suitable alignment layers are known in the art, like for example rubbed polyimide or alignment layers prepared by photoalignment as described in U.S. Pat. No. 5,602,661, U.S. Pat. No. 5,389,698 or U.S. Pat. No. 6,717,644.

It is also possible to induce or improve alignment by annealing the polymerizable LC material at elevated temperature, preferably at its polymerization temperature, prior to polymerization.

Polymerization is achieved for example by exposing the polymerizable material to heat or actinic radiation. Actinic radiation means irradiation with light, like UV light, IR light or visible light, irradiation with X-rays or gamma rays or irradiation with high energy particles, such as ions or electrons. Preferably polymerization is carried out by UV irradiation. As a source for actinic radiation for example a single UV lamp or a set of UV lamps can be used. When using a high lamp power the curing time can be reduced. Another possible source for actinic radiation is a laser, like for example a UV, IR or visible laser.

Polymerization is preferably carried out in the presence of an initiator absorbing at the wavelength of the actinic radiation. For example, when polymerizing by means of UV light, a photoinitiator can be used that decomposes under UV irradiation to produce free radicals or ions that start the polymerization reaction. For polymerizing acrylate or methacrylate groups preferably a radical photoinitiator is used. For polymerizing vinyl, epoxide or oxetane groups preferably a cationic photoinitiator is used. It is also possible to use a thermal polymerization initiator that decomposes when heated to produce free radicals or ions that start the polymerization. Typical radicalic photoinitiators are for example the commercially available Irgacure® or Darocure® (Ciba Geigy AG, Basel, Switzerland). A typical cationic photoinitiator is for example UVI 6974 (Union Carbide).

The polymerizable material may also comprise one or more stabilizers or inhibitors to prevent undesired spontaneous polymerization, like for example the commercially available Irganox® (Ciba Geigy AG, Basel, Switzerland).

The curing time depends, inter alia, on the reactivity of the polymerizable material, the thickness of the coated layer, the type of polymerization initiator and the power of the UV lamp. The curing time is preferably ≦5 minutes, very preferably ≦3 minutes, most preferably ≦1 minute. For mass production short curing times of ≦30 seconds are preferred.

Preferably polymerization is carried out in an inert gas atmosphere like nitrogen or argon.

The polymerizable material may also comprise one or more dyes having an absorption maximum adjusted to the wavelength of the radiation used for polymerization, in particular UV dyes like e.g. 4,4"-azoxy anisole or Tinuvin® dyes (from Ciba AG, Basel, Switzerland).

In another preferred embodiment the polymerizable material comprises one or more monoreactive polymerizable non-mesogenic compounds, preferably in an amount of 0 to 50%, very preferably 0 to 20%. Typical examples are alkylacrylates or alkylmethacrylates.

In another preferred embodiment the polymerizable material comprises one or more di- or multireactive polymerizable non-mesogenic compounds, preferably in an amount of 0 to 50%, very preferably 0 to 20%, alternatively or in addition to the di- or multireactive polymerizable mesogenic compounds. Typical examples of direactive non-mesogenic compounds are alkyldiacrylates or alkyldimethacrylates with alkyl groups of 1 to 20 C atoms. Typical examples of multi-reactive non-mesogenic compounds are trimethylpropanetri-methacrylate or pentaerythritoltetraacrylate.

It is also possible to add one or more chain transfer agents to the polymerizable material in order to modify the physical properties of the polymer film. Especially preferred are thiol compounds, for example monofunctional thiols like dodecane thiol or multifunctional thiols like trimethylpropane tri (3-mercaptopropionate). Very preferred are mesogenic or LC thiols as disclosed for example in WO 96/12209, WO 96/25470 or U.S. Pat. No. 6,420,001. By using chain transfer agents the length of the free polymer chains and/or the length of the polymer chains between two crosslinks in the polymer film can be controlled. When the amount of the chain transfer agent is increased, the polymer chain length in the polymer film decreases.

The polymerizable material may also comprise a polymeric binder or one or more monomers capable of forming a polymeric binder, and/or one or more dispersion auxiliaries. Suitable binders and dispersion auxiliaries are disclosed for example in WO 96/02597. Preferably, however, the polymerizable material does not contain a binder or dispersion auxiliary.

The polymerizable material can additionally comprise one or more additional components like for example catalysts, sensitizers, stabilizers, inhibitors, chain-transfer agents, co-reacting monomers, surface-active compounds, lubricating agents, wetting agents, dispersing agents, hydrophobing agents, adhesive agents, flow improvers, defoaming agents, deaerators, diluents, reactive diluents, auxiliaries, colourants, dyes or pigments.

The thickness of a polymer film according to the present invention is preferably from 0.3 to 5 microns, very preferably from 0.5 to 3 microns, most preferably from 0.7 to 1.5 microns. For use as alignment layer, thin films with a thickness of 0.05 to 1, preferably 0.1 to 0.4 microns are preferred.

The polymer film of the present invention can be used as retardation or compensation film for example in LCDs to improve the contrast and brightness at large viewing angles and reduce the chromaticity. It can be used outside the switchable LC cell of the LCD or between the substrates, usually glass substrates, forming the switchable LC cell and containing the switchable LC medium (incell application).

The polymer film of the present invention can also be used as alignment layer for LC materials. For example, it can be used in an LCD to induce or improve alignment of the switchable LC medium, or to align a subsequent layer of polymerizable LC material coated thereon. In this way, stacks of polymerized LC films can be prepared.

In particular, the chiral compounds, mixtures, polymers and polymer films according to the present invention can be used in reflective polarizers as disclosed in GB 2 315 072 or WO 97/35219, negative C plate retarders as disclosed in WO 01/20394 or WO 2004/013666, biaxial negative C plate retarders as disclosed in WO 2003/054111, alignment layers as disclosed in EP 1 376 163, birefringent markings or images for decorative or security use as disclosed in GB 2 315 760, WO 02/85642, EP 1 295 929 or EP 1 381 022.

The polymer film of the present invention can be used in conventional LC displays, for example displays with vertical alignment like the DAP (deformation of aligned phases), ECB (electrically controlled birefringence), CSH (colour super homeotropic), VA (vertically aligned), VAN or VAC (vertically aligned nematic or cholesteric), MVA (multi-domain vertically aligned) or PVA (patterned vertically aligned) mode; displays with bend or hybrid alignment like the OCB (optically compensated bend cell or optically compensated birefringence), R—OCB (reflective OCB), HAN (hybrid aligned nematic) or pi-cell (π-cell) mode; displays with twisted alignment like the TN (twisted nematic), HTN (highly twisted nematic), STN (super twisted nematic), AMD-TN (active matrix driven TN) mode; displays of the IPS (in plane switching) mode, or displays with switching in an optically isotropic phase or in the blue phase, as described for example in WO 02/93244.

Especially preferred are TN, STN, VA and IPS displays, in particular those of the active-matrix type. Further preferred are transflective displays.

In the foregoing and the following, all temperatures are given in degrees Celsius, and all percentages are by weight, unless stated otherwise. The following abbreviations are used to illustrate the LC phase behaviour: C, K=crystalline; N=nematic; S=smectic; N*, Ch=chiral nematic or cholesteric; I=isotropic. The numbers between these symbols indicate the phase transition temperatures in degree Celsius. Furthermore, mp is the melting point and cp is the clearing point (in ° C.).

Unless stated otherwise, the precentages of components of a polymerizable mixture as given above and below refer to the total amount of solids in the mixture polymerizable mixture, i.e. not including solvents.

The HTP of a chiral dopant in an LC host material is given as HTP=(p*c)$^{-1}$ (in μm$^{-1}$), wherein p is the pitch of the molecular helix (in μm) and c is the concentration (in wt. %) of the chiral compound in the host (a concentration of 1% by weight for example corresponds to c=0.01). Unless stated otherwise, specific HTP values given above and below relate to a dopant concentration of 1% in the LC host mixture MLC-6260 (Merck KGaA, Darmstadt, Germany) at 20° C.

The examples below shall illustrate the invention without limiting it. The mirror images (either S,S- or R,R-isomer) of all the binaphthyl compounds shown in the examples can also be prepared according or in analogy to the methods described.

EXAMPLE 1

Compound (1) is prepared according to reaction scheme 2 below.

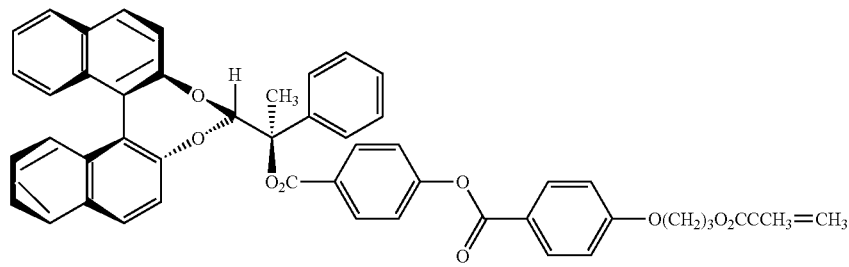

(1)

Scheme 2:

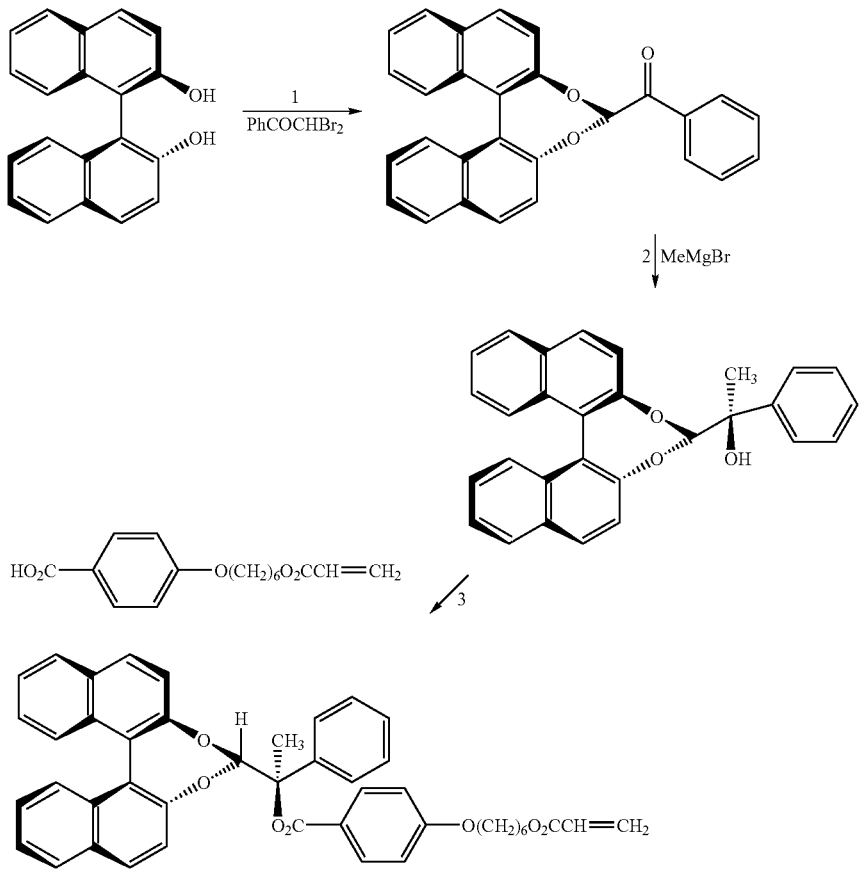

Step 1: Sodium salt of S-(−)-1,1'-bi(2-naphthol) is formed from the reaction of sodium hydride (60% suspension in toluene) in dimethylformamide, then reacted with dibromoacetophenone to form a ketone. Only a single isomer is produced due to the $C_2$-symmetry of the binaphthol moiety.

Step 2: Addition of a methyl group is achieved under typical Grignard conditions, i.e. addition of methyl magnesium bromide in tetrahydrofuran solvent at −78° C. warming to room temperature giving a single distereoisomer and a free hydroxyl group.

Step 3: Esterification of the free hydroxyl group is achieved by reaction of an acid using dicyclohexylcarbodiimide (1 equiv.), and a catalytic amount of dimethylaminopyridine in dichloromethane at room temperature.

The following compounds are prepared analoguously:

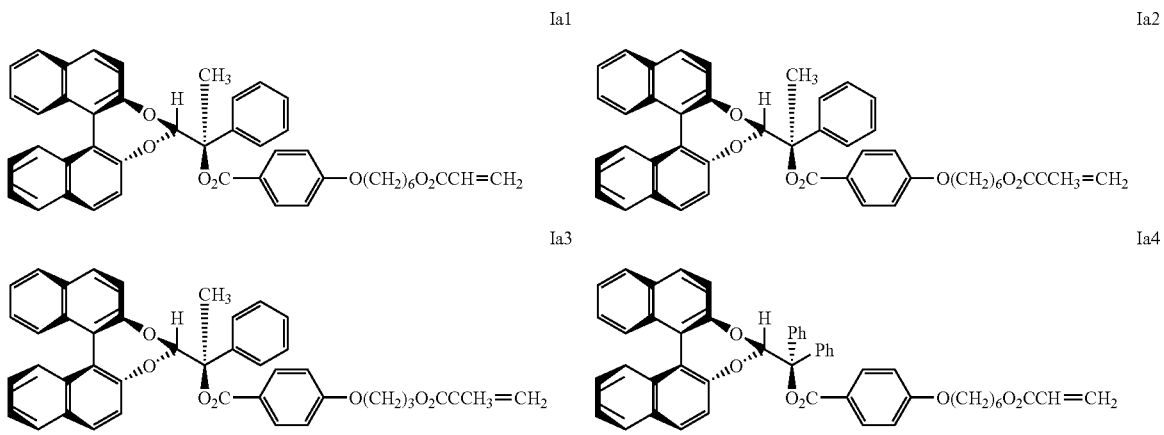

-continued
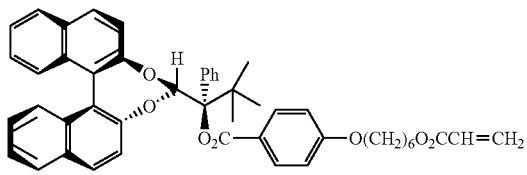
Ia5
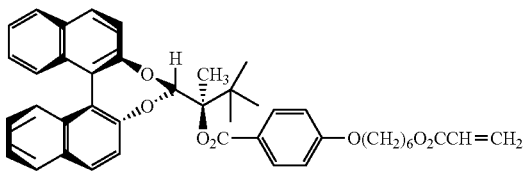
Ia6
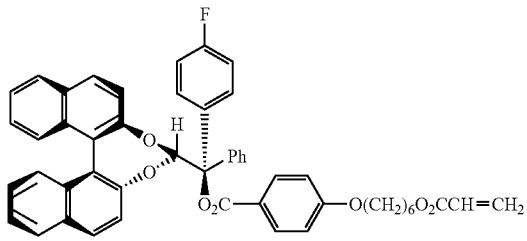
Ia7
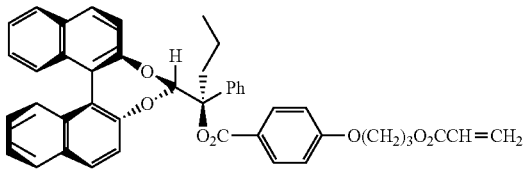
Ia8
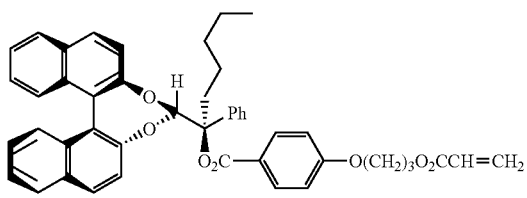
Ia9
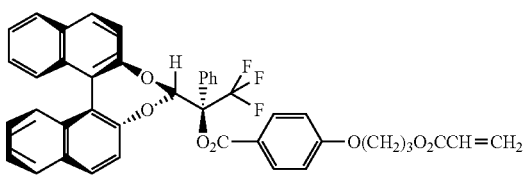
Ia10
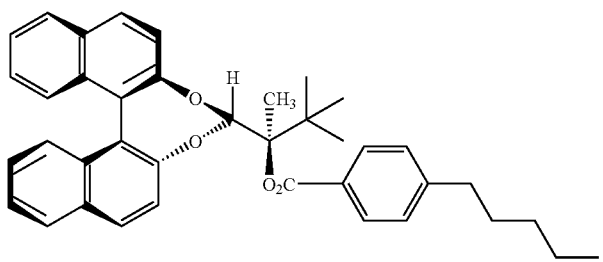
Ib1
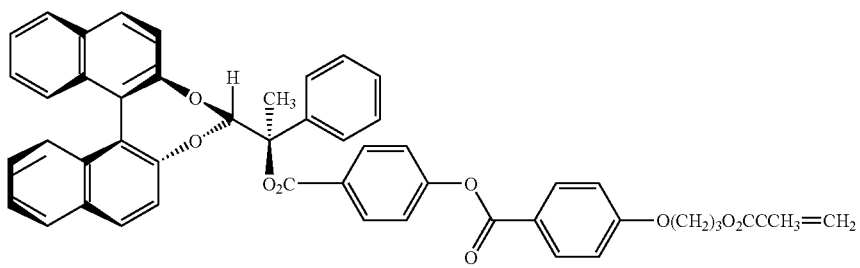
Ic1
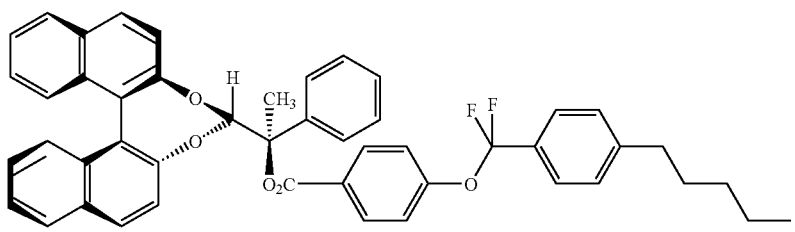
Id1

-continued

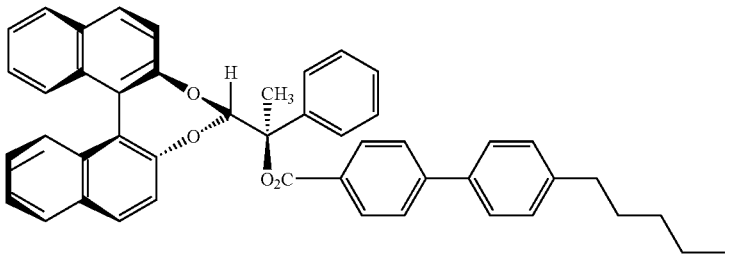
Id2

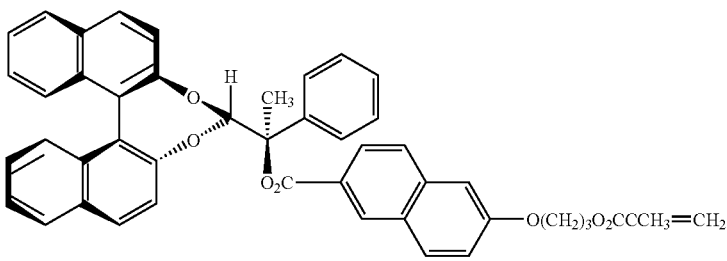
Ie1

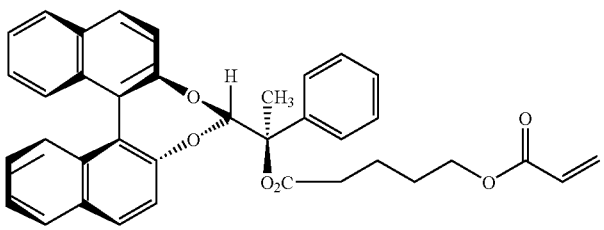
Ig1

The invention claimed is:

1. A compound of formula I

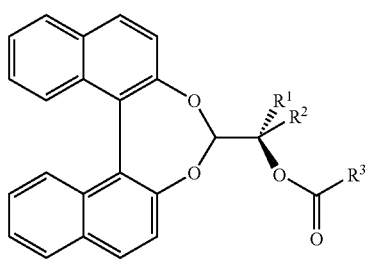
I wherein $R^1$ and $R^2$ are different groups selected from H, halogen, —CN, —NC, —NCO, —NCS, —OCN, —SCN, —C(=O)NR°R°°, —C(=O)Y, —C(=O)R°, —NH$_2$, —NR°R°°, —SH, —SR°, —SO$_3$H, —SO$_2$R°, —OH, —NO$_2$, —CF$_3$, —SF$_5$, P-Sp-X—, a mono- or polynuclear aryl or heteroaryl with 5 to 40 C atoms that is optionally substituted, or a straight-chain, branched or cyclic alkyl with 1 to 25 C-atoms which is unsubstituted, mono- or polysubstituted by F, Cl, Br, I or CN, and wherein one or more non-adjacent CH$_2$ groups are optionally replaced, in each case independently from one another, by —O—, —S—, —NH—, —NR°—, —SiR°R°°—, —CO—, —COO—, —OCO—, —O—CO—O—, —S—CO—, —CO—S—, —CO—NR°—, —NR°—CO—, —NR°—CO—NR°°—, —CY$^1$=CY$^2$— or —C≡C— in such a manner that O and/or S atoms are not linked directly to one another, $R°$ and $R°°$ are independently of each other H, straight-chain, branched or cyclic alkyl with 1 to 12 C atoms, or aryl with 6 to 12 C atoms, Y is halogen, $R^3$ is —(Z$^1$-A$^1$)$_m$—R$^4$, $R^4$ is H, halogen, —CN, —NC, —NCO, —NCS, —OCN, —SCN, —C(=O)NR°R°°, —C(=O)Y, —C(=O)R°, —NH$_2$, —NR°R°°, —SH, —SR°, —SO$_3$H, —SO$_2$R°, —OH, —NO$_2$, —CF$_3$, —SF$_5$, P-Sp-X—, a mono- or polynuclear aryl or heteroaryl with 5 to 40 C atoms that is optionally substituted, or a straight-chain, branched or cyclic alkyl with 1 to 25 C-atoms which is unsubstituted, mono- or polysubstituted by F, Cl, Br, I or CN, and wherein one or more non-adjacent CH$_2$ groups are optionally replaced, in each case independently from one another, by —O—, —S—, —NH—, —NR°—, —SiR°R°°—, —CO—, —COO—, —OCO—, —O—CO—O—, —S—CO—, —CO—S—, —CO—NR°—, —NR°—CO—, —NR°—CO—NR°°—, —CY$^1$=CY$^2$— or —C≡C— in such a manner that O and/or S atoms are not linked directly to one another, m is 0,1,2,3 or 4, $A^1$ is in case of multiple occurrence independently of one another an aromatic or alicyclic group, which optionally contains one or more hetero atoms selected from N, O and S, and is optionally mono- or polysubstituted by H, halogen, —CN, —NC, —NCO, —NCS, —OCN, —SCN, —C(=O)NR°R°°, —C(=O)Y, —C(=O)R°, —NH$_2$, —NR°R°°, —SH, —SR°, —SO$_3$H, —SO$_2$R°, —OH, —NO$_2$, —CF$_3$, —SF$_5$, P-Sp-X—, a mono- or polynuclear aryl or heteroaryl with 5 to 40 C atoms that is optionally substituted, or a straight-chain, branched or cyclic alkyl with 1 to 25 C-atoms which is unsubstituted, mono- or polysubstituted by F, Cl, Br, I or CN, and wherein one or more non-adjacent CH$_2$ groups are optionally replaced, in each case independently from one another, by —O—, —S—, —NH—, —NR$^o$—, —SiR$^o$R$^{oo}$—, —CO—, —COO—, —OCO—, —O—CO—O—, —S—CO—, —CO—S—, —CO—NR$^o$—, —NR$^o$—CO—, —NR$^o$—CO—NR$^{oo}$—, —CY$^1$=CY$^2$— or —C≡C— in such a manner that O and/or S atoms are not linked directly to one another, Z is in case of multiple occurrence independently of one another —O—, —S—, —CO—, —COO—, —OCO—, —S—CO—, —CO—S—, —O—COO—, —CO—NR$^o$—, —NR$^o$—CO—, —NR$^o$—CO—NR$^{oo}$, —NR$^o$—CO—O—, —O—CO—NR$^o$—, —OCH$_2$—, —CH$_2$O—, —SCH$_2$—, —CH$_2$S—, —CF$_2$O—, —OCF$_2$—, —CF$_2$S—, —SCF$_2$—, —CH$_2$CH$_2$—, —(CH$_2$)$_4$—, —CF$_2$CH$_2$—, —CH$_2$CF$_2$—, —CF$_2$CF$_2$—, —CH=N—, —N=CH—, —N=N—, —CH=CR$^o$—, —CY$^1$=CY$^2$—, —C≡C—, —CH=CH—COO—, —OCO—CH=CH— or a single bond, Y$^1$ and Y$^2$ are independently of each other H, F, Cl or CN, P is a polymerizable group, Sp is a spacer group or a single bond, X is —O—, —S—, —CO—, —COO—, —OCO—, —O—COO—, —CO—NR$^o$—, —NR$^o$—CO—, —NR$^o$—CO—NR$^o$—, —OCH$_2$—, —CH$_2$O—, —SCH$_2$—, —CH$_2$S—, —CF$_2$O—, —OCF$_2$—, —CF$_2$S—, —SCF$_2$—, —CF$_2$CH$_2$—, —CH$_2$CF$_2$—, —CF$_2$CF$_2$—, —CH=N—, —N=CH—, —N=N—, —CH=CR$^o$—, —CY$^1$=CY$^2$—, —C≡C—, —CH=CH—COO—, —OCO—CH=CH— or a single bond, wherein R$^1$ and R$^2$ are different from —O—CO—R$^3$ and the binaphthyl group is optionally substituted by one or more groups R$^1$ or R$^3$.

2. A compound according to claim 1, wherein A$^1$ and said mono- or polynuclear aryl or heteroaryl in the definitions of R$^1$, R$^2$, and R$^4$ are each an aromatic group which optionally contains one or more hetero atoms selected from N, O and S, and which is optionally mono- or polysubstituted by L; and L is F, Cl, Br, I, —CN, —NO$_2$, —NCO, —NCS, —OCN, —SCN, —C(=O)NR$^o$R$^{oo}$, —C(=O)X, —C(=O)R$^o$, —NR$^o$R$^{oo}$, —OH, —SF$_5$, or straight chain or branched alkyl, alkoxy, alkylcarbonyl, alkoxycarbonyl, alkylcarbonlyoxy or alkoxycarbonyloxy, in each case having up to 12 C atoms and one or more H atoms are optionally replaced by F or Cl.

3. A compound according to claim 1, wherein

A$^1$ is selected from 1,4-phenylene, pyridine- 2,5-diyl, pyrimidine-2,5-diyl, thiophene -2,5-diyl, naphthalene-2,6-diyl, 1,2,3,4-tetrahydro-naphthalene-2,6-diyl, indane-2,5-diyl, 1,4-cyclohexylene, bicyclo[2.2.2]octane-1,4-diyl, wherein one or two non-adjacent CH$_2$ groups are optionally replaced by O and/or S, wherein these groups are unsubstituted, mono- or polysubstituted by L; and L is F, Cl, Br, I, —CN, —NO$_2$, —NCO, —NCS, —OCN, —SCN, —C(=O)NR$^o$R$^{oo}$, —C(=O)X, —C(=O)R$^o$, —NR$^o$R$^{oo}$, —OH, —SF$_5$, or straight chain or branched alkyl, alkylcarbonyl, alkoxycarbonyl, alkylcarbonlyoxy or alkoxycarbonyloxy, in each case having up to 12 C atoms and one or more H atoms are optionally replaced by F or Cl.

4. A compound according to claim 1, wherein R$^1$ and/or R$^2$ is alkyl having 1 to 20 C atoms which is optionally fluorinated, or optionally substituted aryl having 1 to 12 C atoms, or one or more of R$^1$, R$^2$ and R$^4$ is P-Sp-X—.

5. A compound according to claim 1, wherein —(Z$^1$-A$^1$)$_m$— is selected from the following formulae and their mirror images

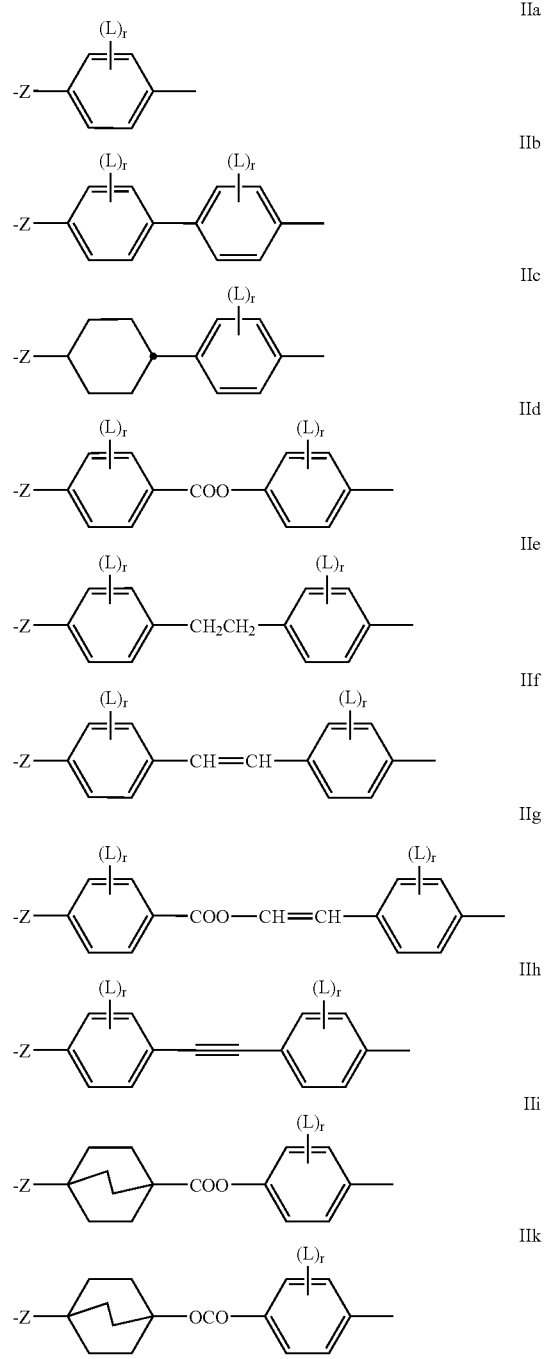

wherein

L is F, Cl, Br, I, —CN, —NO$_2$, —NCO, —NCS, —OCN, —SCN, —C(=O)NR$^o$R$^{oo}$, —C(=O)X, —C(=O)R$^o$, —NR$^o$R$^{oo}$, —OH, —SF$_5$, or straight chain or branched alkyl, alkoxy, alkylcarbonyl, alkoxycarbonyl, alkylcarbonlyoxy or alkoxycarbonyloxy, in each case having up to 12 C atoms and one or more H atoms are optionally replaced by F or Cl, Z is —O—, —S—, —CO—, —COO—, —OCO—, —S—CO—, —CO—S—, —O—COO—, —CO—NR⁰—, —NR⁰—CO—, —NR⁰—CO—NR⁰⁰, —NR⁰—CO—O—, —O—CO—NR⁰—, —OCH₂—, —CH₂O—, —SCH₂—, —CH₂S—, —CF₂O—, —OCF₂—, —CF₂S—, —SCF₂—, —CH₂CH₂—, —(CH₂)₄—, —CF₂CH₂—, —CH₂CF₂—, —CF₂CF₂—, —CH=N—, —N=CH—, —N=N—, —CH=CR⁰—, —CY¹=CY²—, —C≡C—, —CH=CH—COO—, —OCO—CH=CH— or a single bond, and r is 0, 1, 2, 3 or 4.

6. A compound according to claim 1, wherein said compound is selected from the following formulae Ia
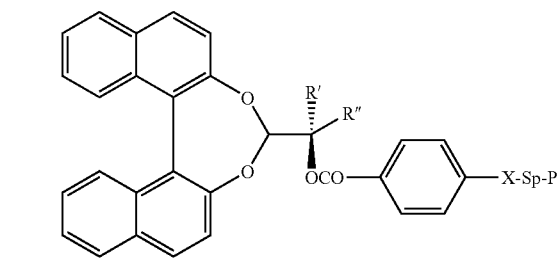

Ib
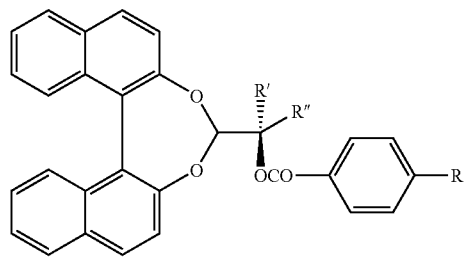

Ic
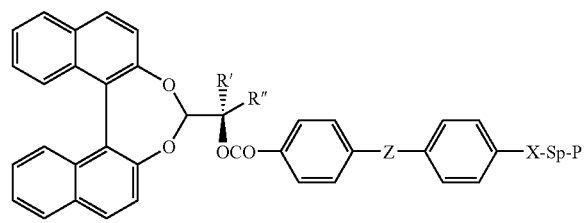

Id
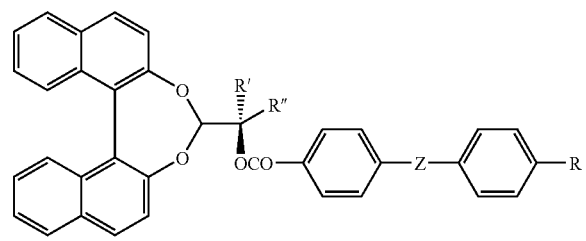

Ie
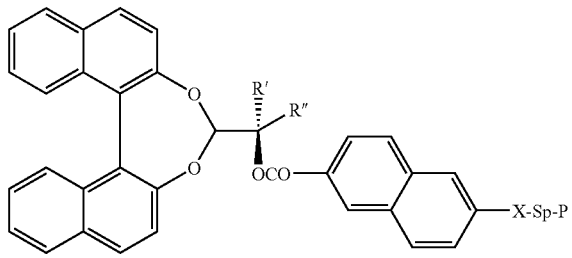

If
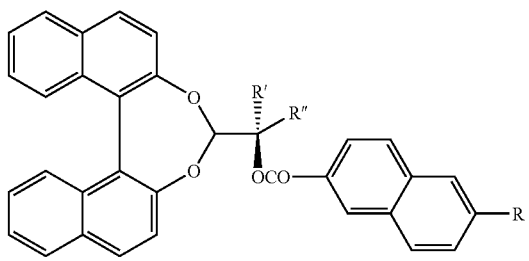

Ig
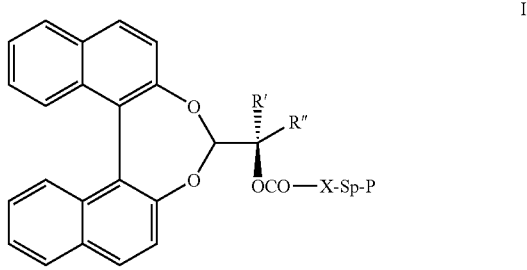

Ih
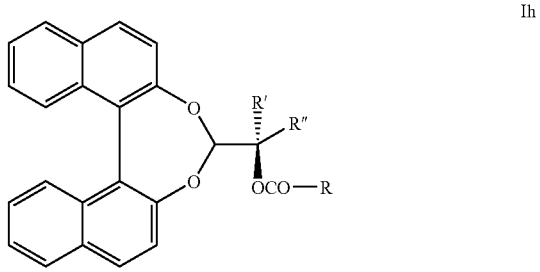

wherein
binaphthyl, naphthyl and phenyl groups are optionally substituted by one or more groups L, R' and R" are different groups selected from optionally fluorinated alkyl having 1 to 12 C atoms, and optionally substituted aryl having 1 to 12 C atoms, Z is —O—, —S—, —CO—, —COO—, —OCO—, —S—CO—, —CO—S—, —O—COO—, —CO—NR⁰—, —NR⁰—CO—, —NR⁰—CO—NR⁰⁰, —NR⁰—CO—O—, —O—CO—NR⁰—, —OCH₂—, —CH₂O—, —SCH₂—, —CH₂S—, —CF₂O—, —OCF₂—, —CF₂S—, —SCF₂—, —CH₂CH₂—, —(CH₂)₄—, —CF₂CH₂—, —CH₂CF₂—, —CF₂CF₂—, —CH=N—, —N=CH—, —N=N—, —CH=CR⁰—, —CY¹=CY²—, —C≡C—, —CH=CH—COO—, —OCO—CH=CH— or a single bond, R is optionally fluorinated alkyl with 1 to 12 C atoms, optionally fluorinated alkoxy with 1 to 12 C atoms, or alkenyl with 2 to 7 C atoms, and L is F, Cl, Br, I, —CN, —NO$_2$, —NCO, —NCS, —OCN, —SCN, —C(=O)NR$^0$R$^{00}$, —C(=O)X, —C(=O)R$^0$, —NR$^0$R$^{00}$, —OH, —SF$_5$, or straight chain or branched alkyl, alkoxy, alkylcarbonyl, alkoxycarbonyl, alkylcarbonlyoxy or alkoxycarbonyloxy, in each case having up to 12 C atoms and one or more H atoms are optionally replaced by F or Cl.

7. A liquid crystal mixture comprising at least two compounds, wherein said mixture, comprises at least one compound according to claim 1.

8. A polymer obtained by polymerizing a compound according to claim 1 in the liquid crystal phase and/or in an oriented state.

9. A method of making electrooptical displays, LCDs, optical films, polarizers, compensators, beam splitters, reflective films, alignment layers, colour filters, holographic elements, hot stamping foils, coloured images, decorative or security markings, LC pigments, adhesives, cosmetics, diagnostics, nonlinear optics, optical information storage, electronic devices, organic semiconductors, field effect transistors (FET), components of integrated circuitry (IC), thin film transistors (TFT), Radio Frequency Identification (RFID) tags, organic light emitting diodes (OLED), electroluminescent displays, lighting devices, photovoltaic devices, sensor devices, electrode materials, photoconductors, electrophotographic recording, lasing materials or devices, comprising employing a compound of claim 1.

10. A liquid crystal display, color filter, polarizer, retardation film, alignment layer, authentification, verification or security marking, coloured image, object or document of value comprising a compound, according to claim 1.

11. A method of preparing a compound according to claim 1, said method comprising:
a) reacting the sodium salt of binaphthol with a dibromoacetophenone moiety to form a ketone,
b) reacting said ketone with an alkyl Grignard reagent to form a hydroxyl intermediate,
c) esterifying the OH group of said hydroxyl intermediate by an acid in the presence of dicyclohexylcarbodiimide and dimethylaminopyridine or by an acid chloride in the presence of a base to give the desired chiral product.

12. An anisotropic polymer film obtained by polymerizing a mixture according to claim 7 in the liquid crystal phase and/or in an oriented state.

13. A compound according to claim 1, wherein
R$^1$ and/or R$^2$ is optionally fluorinated alkyl having 1 to 20,
R$^1$ and/or R$^2$ is optionally substituted aryl having 1 to 12 C atoms,
R$^1$ and/or R$^2$ is P-Sp-X—,
the compound comprises at least one group P-Sp-X—,
the binaphthyl group is substituted by R$^1$ or R$^3$,
R$^4$ is P-Sp-X—,
m is 0, or
m is 1 or 2.

14. A compound according to claim 1, wherein
A$^1$ is furan, pyrrol, thiophene, oxazole, thiazole, thiadiazole, imidazole, phenylene, cyclohexylene, cyclohexenylene, bicyclooctane, pyridine, pyrimidine, pyrazine, azulene, indane, naphthalene, tetrahydronaphthalene, anthracene, or phenanthrene, which in each case is optionally substituted by one or more groups L, or
A$^1$ is 1,4-phenylene, pyridine-2,5-diyl, pyrimidine-2,5-diyl, thiophene-2,5-diyl, naphthalene-2,6-diyl, 1,2,3,4-tetrahydro-naphthalene-2,6-diyl, indane-2,5-diyl, 1,4-cyclohexylene, bicyclo[2.2.2]octane-1,4-diyl, wherein in each case one or two non-adjacent CH$_2$ groups are each optionally replaced by O and/or S, and which in each case is unsubstituted, or mono- or polysubstituted by L, and L is F, Cl, Br, I, —CN, —NO$_2$, —NCO, —NCS, —OCN, —SCN, —C(=O)NR$^0$R$^{00}$, —C(=O)X, —C(=O)R$^0$, —NR$^0$R$^{00}$, —OH, —SF$_5$, or straight chain or branched alkyl with 1 to 12 C atoms, alkoxy with 1 to 12 C atoms, alkylcarbonyl with up to 12 C atoms, alkoxycarbonyl with up to 12 C atoms, alkylcarbonlyoxy with up to 12 C atoms, or alkoxycarbonyloxy, in each case having up to 12 C atoms and one or more H atoms are optionally replaced by F or Cl.

15. A compound according to claim 1, wherein
P is selected CH$_2$=CW$^1$—

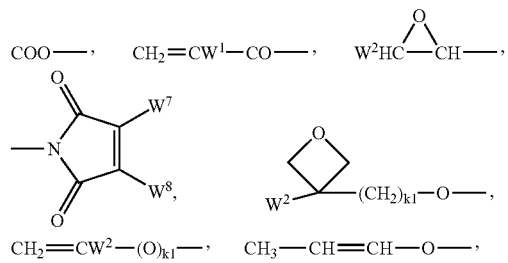

CH$_2$=CW$^2$—(O)$_{k1}$—,  CH$_3$—CH=CH—O—, (CH$_2$=CH)$_2$CH—OCO—, (CH$_2$=CH—CH$_2$)$_2$CH—OCO—, (CH$_2$=CH)$_2$CH—O—, (CH$_2$=CH—CH$_2$)$_2$N—, (CH$_2$=CH—CH$_2$)$_2$N—CO—, HO—CW$^2$W$^3$—, HS—CW$^2$W$^3$—, HW$^2$N—, HO—CW$^2$W$^3$—NH—, CH$_2$=CW$^1$—CO—NH—, CH$_2$=CH—(COO)$_{k1}$-Phe-(O)$_{k2}$-, CH$_2$=CH—(CO)$_{k1}$-Phe-(O)$_{k2}$-, Phe-CH=CH—, HOOC—, OCN—, and W$^4$W$^5$W$^6$Si—, W$^1$ is H, F, Cl, CN, CF$_3$, phenyl or alkyl with 1 to 5 C-atoms, W$^2$ and W$^3$ are each independently H or alkyl with 1 to 5 C-atoms, W$^4$, W$^5$ and W$^6$ are each independently Cl, oxaalkyl with 1 to 5 C-atoms, or oxacarbonylalkyl with 1 to 5 C-atoms, W$^7$ and W$^8$ are each independently H, Cl or alkyl with 1 to 5 C-atoms, Phe is 1,4-phenylene which is optionally substituted by one or more groups L, k$_1$ and k$_2$ are each independently 0 or 1, and L is F, Cl, Br, I, —CN, —NO$_2$, —NCO, —NCS, —OCN, —SCN, —C(=O)NR$^0$R$^{00}$, —C(=O)X, —C(=O)R$^0$, —NR$^0$R$^{00}$, —OH, —SF$_5$, optionally substituted silyl, or aryl with up to 12 C atoms, or straight chain or branched alkyl with 1 to 12 C atoms, alkoxy with 1 to 12 C atoms, alkylcarbonyl with up to 12 C atoms, alkoxycarbonyl with up to 12 C atoms, alkylcarbonlyoxy with up to 12 C atoms, or alkoxycarbonyloxy with up to 12 C atoms, wherein one or more H atoms are optionally replaced by F or Cl.

16. A compound according to claim 15, wherein P is selected from CH$_2$=CH—COO—, CH$_2$=C(CH$_3$)—COO—, CH$_2$=CH—, CH$_2$=CH—O—, (CH$_2$=CH)$_2$CH—OCO—, (CH$_2$=CH)$_2$CH—O—,

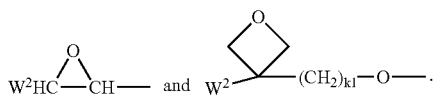

17. A compound according to claim 1, wherein Sp is alkylene with 1 to 20 C atoms which is optionally mono- or polysubstituted by F, Cl, Br, I or CN, and wherein one or more non-adjacent CH$_2$ groups are optionally replaced, in each case independently from one another, by —O—, —S—, —NH—, —NR$^0$—, —SiR$^0$R$^{00}$—, —CO—, —COO—, —OCO—, —OCO—O—, —S—CO—, —CO—S—, —NR$^0$—CO—O—, —O—CO—NR$^0$—, —NR$^0$—CO—NR$^0$—, —CH═CH— or —C≡C— in such a manner that O and/or S atoms are not linked directly to one another.

18. A compound according to claim 15, wherein Sp is alkylene with 1 to 20 C atoms which is optionally mono- or polysubstituted by F, Cl, Br, I or CN, and wherein one or more non-adjacent CH$_2$ groups are optionally replaced, in each case independently from one another, by —O—, —S—, —NH—, —NR$^0$—, —SiR$^0$R$^{00}$—, —CO—, —COO—, —OCO—, —OCO—O—, —S—CO—, —CO—S—, —NR$^0$—CO—O—, —O—CO—NR$^0$—, —NR$^0$—CO—NR$^0$—, —CH═CH— or —C≡C— in such a manner that O and/or S atoms are not linked directly to one another.

19. A compound according to claim 18, wherein Sp is —(CH$_2$)$_p$—, —(CH$_2$CH$_2$O)$_q$—CH$_2$CH$_2$—, —CH$_2$CH$_2$—S—CH$_2$CH$_2$—, —CH$_2$CH$_2$—NH—CH$_2$CH$_2$—, or —(SiR$^0$R$^{00}$—O)$_p$—, P is an integer from 2 to 12, and q is an integer from 1 to 3.

20. A compound according to claim 18, wherein Sp is ethylene, propylene, butylene, pentylene, hexylene, heptylene, octylene, nonylene, decylene, undecylene, dodecylene, octadecylene, ethyleneoxyethylene, methyleneoxy-butylene, ethylene-thioethylene, ethylene-N-methyl-iminoethylene, 1-methylalkylene, ethenylene, propenylene or butenylene.

21. A compound according to claim 5, wherein
P is selected from CH$_2$═CW$^1$—

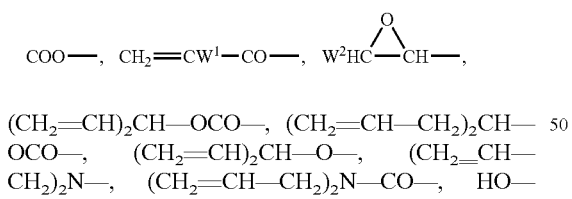

(CH$_2$═CH)$_2$CH—OCO—, (CH$_2$═CH—CH$_2$)$_2$CH—OCO—, (CH$_2$═CH)$_2$CH—O—, (CH$_2$═CH—CH$_2$)$_2$N—, (CH$_2$═CH—CH$_2$)$_2$N—CO—, HO—CW$^2$W$^3$—, HS—CW$^2$W$^3$—, HW$^2$N—, HO—CW$^2$W$^3$—NH—, CH$_2$═CW$^1$—CO—NH—, CH$_2$═CH—(COO)$_{k1}$-Phe-(O)$_{k2}$—, CH$_2$═CH—(CO)$_{k1}$-Phe-(O)$_{k2}$-, Phe-CH═CH—, HOOC—, OCN—, and W$^4$W$^5$W$^6$Si—, W$^1$ is H, F, Cl, CN, CF$_3$, phenyl or alkyl with 1 to 5 C-atoms, W$^2$ and W$^3$ are each independently H or alkyl with 1 to 5 C-atoms, W$^4$, W$^5$ and W$^6$ are each independently Cl, oxaalkyl with 1 to 5 C-atoms, or oxacarbonylalkyl With 1 to 5 C-atoms, W$^7$ and W$^8$ are each independently H, Cl or alkyl with 1 to 5 C-atoms, Phe is 1,4-phenylene which is optionally substituted by one or more groups L, k$_1$ and k$_2$ are each independently 0 or 1, L is F, Cl, Br, I, —CN, —NO$_2$, —NCO, —NCS, —OCN, —SCN, —C(═O)NR$^0$R$^{00}$, —C(═O)X, —C(═O)R$^0$, —NR$^0$R$^{00}$, —OH, —SF$_5$, optionally substituted silyl, or aryl with up to 12 C atoms, or straight chain or branched alkyl with 1 to 12 C atoms, alkoxy with 1 to 12 C atoms, alkylcarbonyl with up to 12 C atoms, alkoxycarbonyl with up to 12 C atoms, alkylcarbonlyoxy with up to 12 C atoms, or alkoxycarbonyloxy with up to 12 C atoms, wherein one or more H atoms are optionally replaced by F or Cl, and Sp is alkylene with 1 to 20 C atoms which is optionally mono- or polysubstituted by F, Cl, Br, I or CN, and wherein one or more non-adjacent CH$_2$ groups are optionally replaced, in each case independently from one another, by —O—, —S—, —NH—, —NR$^0$—, —SiR$^0$R$^{00}$—, —CO—, —COO—, —OCO—, —OCO—O—, —S—CO—, —CO—S—, —NR$^0$—CO—O—, —O—CO—NR$^0$—, —NR$^0$—CO—NR$^0$—, —CH═CH— or —C≡C— in such a manner that O and/or S atoms are not linked directly to one another.

22. A compound according to claim 6, wherein
R' and R" are selected from phenyl, 4-fluorophenyl, methyl, ethyl, n-propyl, i-propyl, t-butyl, n-pentyl and trifluoromethyl, R' is methyl and R" is phenyl, or R" is methyl and R' is phenyl, one of R' and R" is t-butyl and the other is methyl or phenyl, one of R' and R" is phenyl and the other is 4-fluorophenyl, ethyl, n-propyl or trifluoromethyl, or X-Sp-P is —O—(CH$_2$)$_n$—P', wherein P' is acrylate or methacrylate and n is 2, 3, 4, 5, 6, 7 or 8.

23. A compound according to claim 1, wherein said compound is selected from: the following formulae Ia1

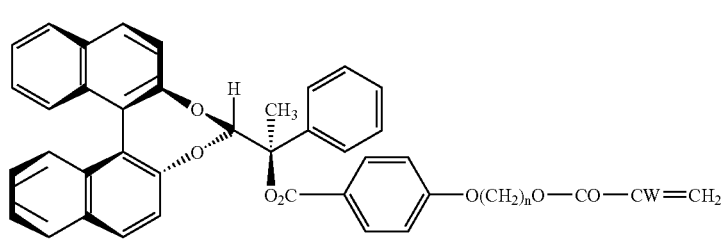

-continued
Ia2
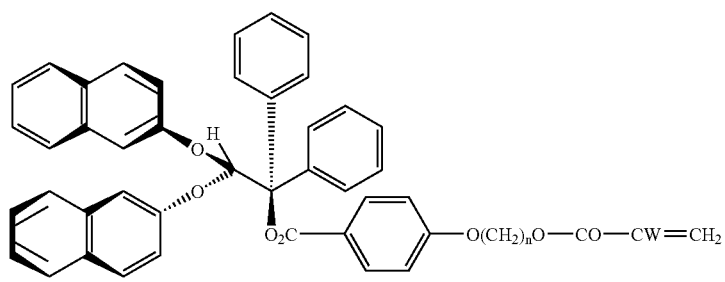
Ia3
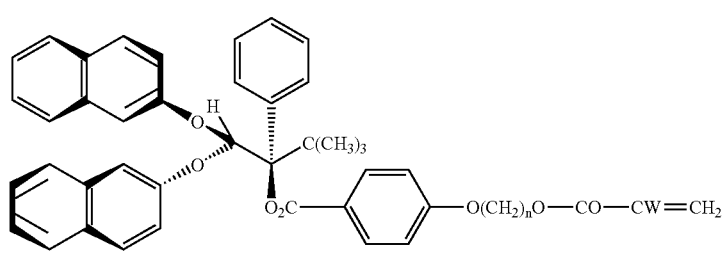
Ia4
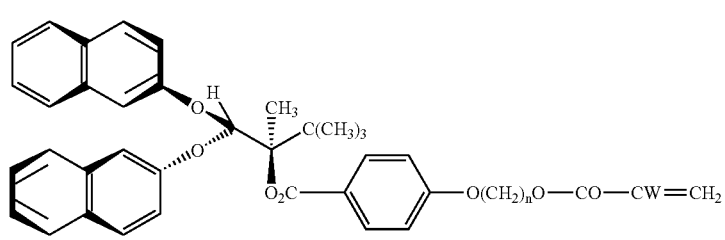
Ia5
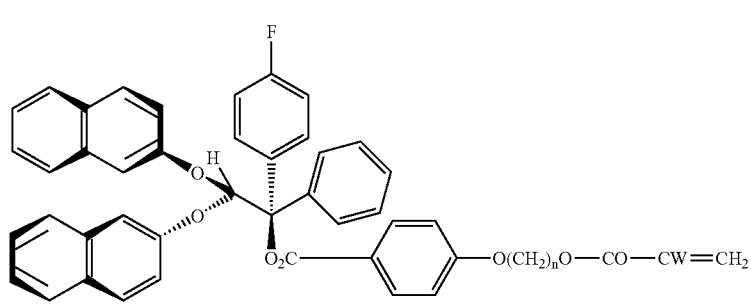
Ia6
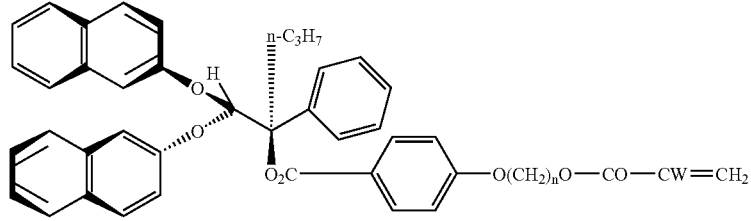
Ia7
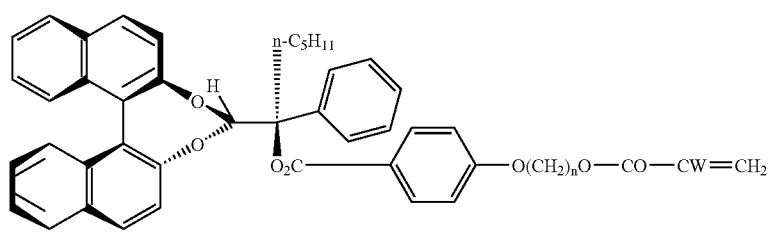

-continued
Ia8
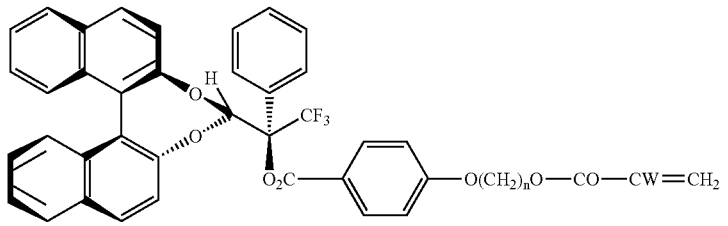
Ib1
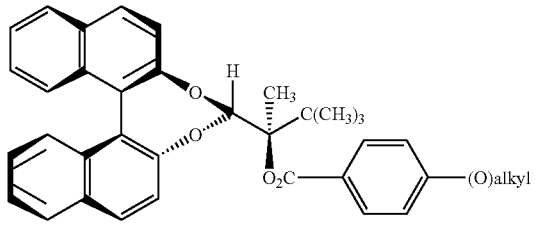
Ic1
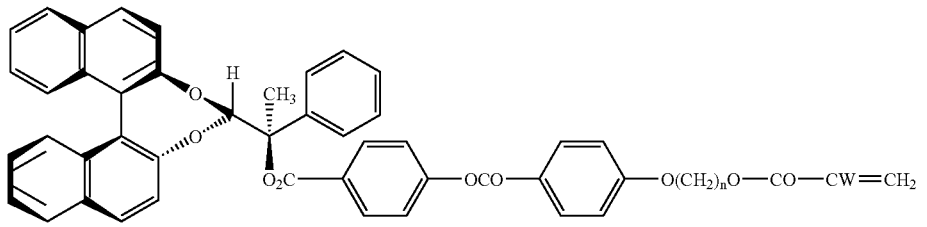
Id1
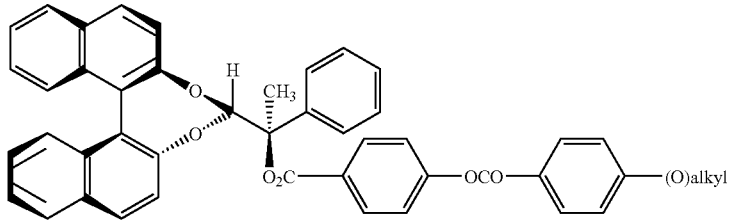
Id2
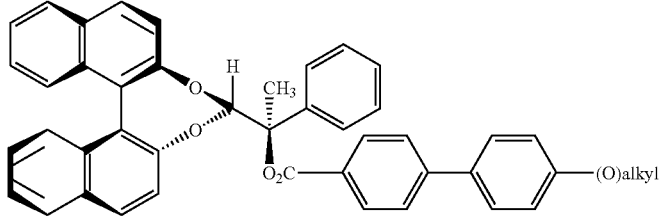
Ie1
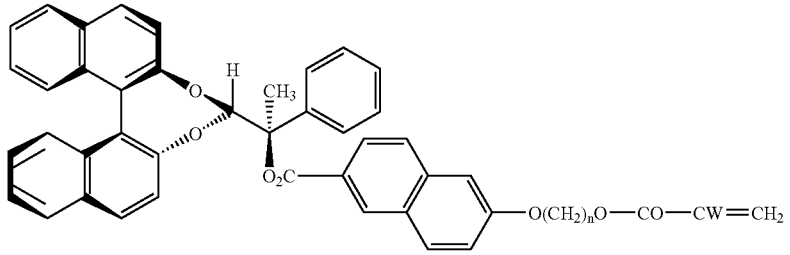

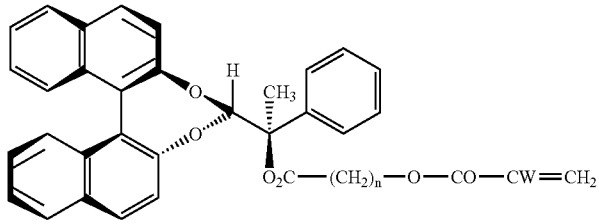

Ig1 wherein the binaphthyl, naphthyl and phenyl groups are optionally substituted by one or more groups L, L is F, Cl, Br, I, —CN, —NO$_2$, —NCO, —NCS, —OCN, —SCN, —C(=O)NR$^0$R$^{00}$, —C(=O)X, —C(=O)R$^0$, —NR$^0$R$^{00}$, —OH, —SF$_5$, or straight chain or branched alkyl, alkoxy, alkylcarbonyl, alkoxycarbonyl, alkylcarbonlyoxy or alkoxycarbonyloxy, in each case having up to 12 C atoms and one or more H atoms are optionally replaced by F or Cl, W is H or CH$_3$, n is 2,3,4,5 or 6, and (O)alkyl is alkyl or alkoxy with 1 to 12 C atoms; and compounds of the above formulae having the mirror images the [1,1']binaphthalenyl-2,2'-diol group.

24. A compound according to claim 16, wherein Sp is alkylene with 1 to 20 C atoms which is optionally mono- or polysubstituted by F, Cl, Br, I or CN, and wherein one or more non-adjacent CH$_2$ groups are optionally replaced, in each case independently from one another, by —O—, —S—, —NH—, —NR$^0$—, —SiR$^0$R$^{00}$—, —CO—, —COO—, —OCO—, —OCO—O—, —S—CO—, —CO—S—, —NR$^0$—CO—O—, —O—CO—NR$^0$—, —NR$^0$—CO—NR$^0$, —CH=CH— or —C≡C— in such a manner that O and/or S atoms are not linked directly to one another.

25. A compound according to claim 24, wherein Sp is —(CH$_2$)$_p$—, —(CH$_2$CH$_2$O)$_q$—CH$_2$CH$_2$—, —CH$_2$CH$_2$—S—CH$_2$CH$_2$—, —CH$_2$CH$_2$—NH—CH$_2$CH$_2$—, or —(SiR$^0$R$^{00}$—O)$_p$—, p is an integer from 2 to 12, and q is an integer from 1 to 3.

26. A compound according to claim 24, wherein Sp is ethylene, propylene, butylene, pentylene, hexylene, heptylene, octylene, nonylene, decylene, undecylene, dodecylene, octadecylene, ethyleneoxyethylene, methyleneoxy-butylene, ethylene-thioethylene, ethylene-N-methyl-iminoethylene, 1-methylalkylene, ethenylene, propenylene or butenylene.

* * * * *

UNITED STATES PATENT AND TRADEMARK OFFICE
CERTIFICATE OF CORRECTION

PATENT NO. : 7,771,800 B2  Page 1 of 1
APPLICATION NO. : 12/088470
DATED : August 10, 2010
INVENTOR(S) : Louise Diane Farrand It is certified that error appears in the above-identified patent and that said Letters Patent is hereby corrected as shown below:

Column 37, lines 13 and 14 reads: "and/or S atoms are not linked directly to one another, -Zis in case of multiple occurrence independently of one"

Should read: -- and/or S atoms are not linked directly to one another, $Z^1$ in case of multiple occurrence independently of one"

Column 43, line 43 reads: "P is selected from $CH_2$_$CW^1$-"

Should read: -- P is selected from $CH_2=CW^1$- --

Column 43, line 49 is blank

Should read: -- 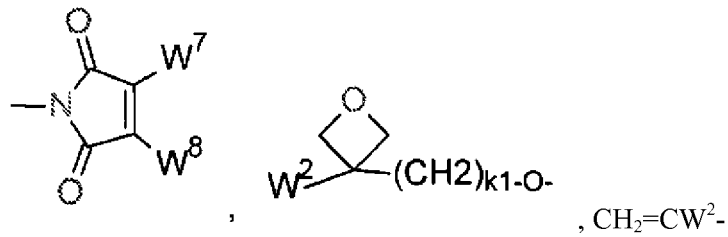 , $CH_2=CW^2$-(O)$_{k1}$-, $CH_3$-CH=CH-O-, --

Column 43; line 52 reads: "OCO-, $(CH_2=CH)_2$CH-O-, $(CH_2$_CH-"

Should read: -- OCO-, $(CH_2=CH)_2$CH-O-, $(CH_2=$CH- --

Signed and Sealed this
Twenty-ninth Day of May, 2012

David J. Kappos
*Director of the United States Patent and Trademark Office*